(12) United States Patent
Grande et al.

(10) Patent No.: US 11,183,625 B2
(45) Date of Patent: Nov. 23, 2021

(54) THERMOCOUPLE DEVICE

(71) Applicant: Micropen Technologies Corporation, Honeoye Falls, NY (US)

(72) Inventors: William J. Grande, Pittsford, NY (US); Lori J. Shaw-Klein, Rochester, NY (US); Min Li, Lima, NY (US)

(73) Assignee: MICROPEN TECHNOLOGIES CORPORATION, Honeoye Falls, NY (US)

( * ) Notice: Subject to any disclaimer, the term of this patent is extended or adjusted under 35 U.S.C. 154(b) by 141 days.

(21) Appl. No.: 15/725,612

(22) Filed: Oct. 5, 2017

(65) Prior Publication Data
US 2018/0033942 A1 Feb. 1, 2018

Related U.S. Application Data

(63) Continuation of application No. 13/051,748, filed on Mar. 18, 2011, now Pat. No. 9,786,829.
(Continued)

(51) Int. Cl.
*H01L 35/32* (2006.01)
*G01K 7/02* (2021.01)
(Continued)

(52) U.S. Cl.
CPC ............... *H01L 35/32* (2013.01); *G01K 7/028* (2013.01); *G01K 13/20* (2021.01); *A61B 18/14* (2013.01);
(Continued)

(58) Field of Classification Search
CPC ......... H01L 35/02; H01L 35/04; H01L 35/12; H01L 35/24; H01L 35/28; H01L 35/30;
(Continued)

(56) References Cited

U.S. PATENT DOCUMENTS 3,099,575 A 7/1963 Hill
3,607,445 A 9/1971 Hines
(Continued)

FOREIGN PATENT DOCUMENTS

WO 2006/002364 A2 1/2006
WO WP2008150006 * 12/2008 ............. H01L 35/32
WO 2009139295 A1 11/2009

OTHER PUBLICATIONS

US 9,786,289 B1, 10/2017, Grande et al. (withdrawn)
(Continued)

*Primary Examiner* — Bethany L Martin
(74) *Attorney, Agent, or Firm* — Troutman Pepper Hamilton Sanders LLP (Rochester)

(57) ABSTRACT

In one aspect, the present invention relates to a thermocouple device comprising a flexible non-planar substrate, a first printed thermocouple element comprising a first metal containing ink composition applied to the flexible non-planar substrate, and a second printed thermocouple element in electrical contact with the first printed thermocouple element making a thermocouple junction. The second printed thermocouple element comprises a second metal containing ink composition with a Seebeck coefficient sufficiently different from the first metal containing ink composition for the first and second printed thermocouple elements to together produce a thermocouple effect. The present application further relates to medical devices comprising the thermocouple and methods of making such devices.

29 Claims, 13 Drawing Sheets

Related U.S. Application Data

(60) Provisional application No. 61/315,534, filed on Mar. 19, 2010.

(51) Int. Cl.
    *G01K 13/20*     (2021.01)
    *A61B 18/14*     (2006.01)
    *A61B 18/00*     (2006.01)
    *A61B 90/00*     (2016.01)

(52) U.S. Cl.
    CPC ............... *A61B 2018/00821* (2013.01); *A61B 2090/3966* (2016.02)

(58) Field of Classification Search
    CPC ........ H01L 35/32; G01K 7/08; G01K 13/002; A61B 18/14
    See application file for complete search history.

(56) References Cited

U.S. PATENT DOCUMENTS

| | | | |
|---|---|---|---|
| 4,004,948 A | | 1/1977 | Smith |
| 4,046,139 A | | 9/1977 | Horn |
| 4,054,478 A | | 10/1977 | Linnon |
| 4,263,921 A | | 4/1981 | Trugillo |
| 4,276,441 A | | 6/1981 | Wilson |
| 4,371,459 A | | 2/1983 | Nazarenko |
| 4,383,534 A | | 5/1983 | Peters |
| 4,438,291 A | | 3/1984 | Eichelberger et al. |
| 4,595,605 A | | 6/1986 | Martin et al. |
| 4,967,759 A | | 11/1990 | Teves |
| 5,192,608 A | | 3/1993 | Haasl et al. |
| 5,295,489 A | | 3/1994 | Bell et al. |
| 5,311,863 A | | 5/1994 | Toppses et al. |
| 5,365,940 A | | 11/1994 | Teves |
| 5,411,600 A | | 5/1995 | Rimai et al. |
| 5,428,249 A | | 6/1995 | Sawayama et al. |
| 5,529,067 A | * | 6/1996 | Larsen ................... A61B 18/02 600/374 |
| 5,540,681 A | | 7/1996 | Strul et al. |
| 5,596,995 A | | 1/1997 | Sherman et al. |
| 5,653,918 A | | 8/1997 | Towlson |
| 5,716,550 A | | 2/1998 | Gardner et al. |
| 5,833,688 A | | 11/1998 | Sieben et al. |
| 5,851,438 A | | 12/1998 | Chan |
| 5,928,571 A | | 7/1999 | Chan |
| 5,967,976 A | * | 10/1999 | Larsen ................... A61B 5/287 600/374 |
| 6,078,830 A | * | 6/2000 | Levin ................. A61B 18/1492 600/374 |
| 6,273,875 B1 | | 8/2001 | Siman et al. |
| 6,292,689 B1 | | 9/2001 | Wallace |
| 6,300,554 B1 | | 10/2001 | Du et al. |
| 6,444,019 B1 | | 9/2002 | Zou et al. |
| 6,450,971 B1 | | 9/2002 | Andrus et al. |
| 6,537,359 B1 | | 3/2003 | Spa |
| 6,627,677 B2 | | 9/2003 | Smith |
| 6,918,391 B1 | | 7/2005 | Moore |
| 6,983,744 B2 | | 1/2006 | Alfery |
| 7,211,205 B2 | | 5/2007 | Conaghan et al. |
| 7,214,410 B2 | | 5/2007 | Szmanda et al. |
| 7,360,437 B2 | | 4/2008 | Hardwicke et al. |
| 2001/0001961 A1 | | 5/2001 | Hiraishi et al. |
| 2003/0084935 A1 | | 5/2003 | Bell |
| 2004/0253185 A1 | | 12/2004 | Herweck et al. |
| 2005/0036020 A1 | | 2/2005 | Li et al. |
| 2005/0076943 A1 | | 4/2005 | Cooper et al. |
| 2005/0257822 A1 | | 11/2005 | Smith et al. |
| 2005/0284483 A1 | | 12/2005 | Patel |
| 2006/0069387 A1 | | 3/2006 | Gedebou |
| 2006/0089637 A1 | | 4/2006 | Werneth et al. |
| 2006/0118121 A1 | | 6/2006 | Martens et al. |
| 2007/0125413 A1 | | 6/2007 | Olsen et al. |
| 2007/0221264 A1 | | 9/2007 | Shutoh et al. |
| 2008/0000387 A1 | | 1/2008 | Renner et al. |
| 2008/0003353 A1 | | 1/2008 | Hardwicke et al. |
| 2008/0039709 A1 | | 2/2008 | Karmarkar |
| 2009/0036304 A1 | | 2/2009 | Misner et al. |
| 2009/0118418 A1 | | 5/2009 | Nakano et al. |
| 2009/0124969 A1 | | 5/2009 | Lenz |
| 2009/0165289 A1 | | 7/2009 | Deng et al. |
| 2009/0217962 A1 | | 9/2009 | Liggett |
| 2009/0227885 A1 | | 9/2009 | Lowery et al. |
| 2009/0277489 A1 | | 11/2009 | Dannoux et al. |
| 2010/0170551 A1 | * | 7/2010 | Hiroyama ............... H01L 35/32 136/205 |
| 2011/0041887 A1 | | 2/2011 | Takahashi |
| 2011/0277803 A1 | | 11/2011 | Grande et al. |

OTHER PUBLICATIONS

Restriction Requirement in U.S. Appl. No. 13/629,356 dated Aug. 13, 2014.
Office Action for U.S. Appl. No. 13/629,356 dated Mar. 11, 2015.
"Material Selection when Printing Functional Traces on Medical Devices . . . " High Beam Research, European Medical Device Technology, May 1, 2010, Shaw-Klein, L. Accessed online Aug. 27, 2015, http://www.highbeam.com/doc/1G1-229677231.html/print.
Advanced Ceramic Materials for Non-Implantable Medical Devices, www.ceramictools.saint-gobain.com.
K. Seshan, Handbook of Thin-Film Deposition Processes and Techniques, Principles, Methods, Equipment and Application, 2d ed., Intel Corporation, Santa Clara, CA (2002).
Medical Devices: Guidance Document, Guidelines for the Classification of Medical Devices (Jul. 2001).
Medical Device Tracking; Guidance for Industry and FDA Staff. US Department of Health and Human Services, Food and Drug Administration, Center for Devices and Radiological http://www.fda.gov/downloads/medicaldevices/deviceregulationandguidance/guidancedocuments/ucm071775.pdf (2010).
http://www.fda.gov/medicaldevices/deviceregulationandguidance/howtomarketyourdevice/investigationaldeviceexemptionIDE/ucm046698.htm (2010), Accessed online Mar. 21, 2017, Internet Archive Wayback Machine.
Office Action for U.S. Appl. No. 13/629,356 dated Sep. 3, 2015.
Office Action for U.S. Appl. No. 13/629,356 dated Sep. 22, 2016.
International Search Report and Written Opinion for PCT/US2011/029029 (dated May 23, 2011).
Thermocouple Application, Precision Analog Applications Seminar (Apr. 11, 2006).
Chen et al., "Dispenser Printed Thermoelectric Energy Generators," Dec. 2009, PowerMEMS 2009, pp. 277-280.
Office Action for U.S. Appl. No. 13/629,356 dated Apr. 4, 2017.
Office Action for U.S. Appl. No. 13/629,356, dated Oct. 27, 2017.
Office Action for U.S. Appl. No. 13/629,356, dated Aug. 6, 2018.
Office Action for U.S. Appl. No. 13/629,356, dated Sep. 25, 2019.
Office Action for U.S. Appl. No. 13/629,356 dated Jul. 17, 2020.

\* cited by examiner

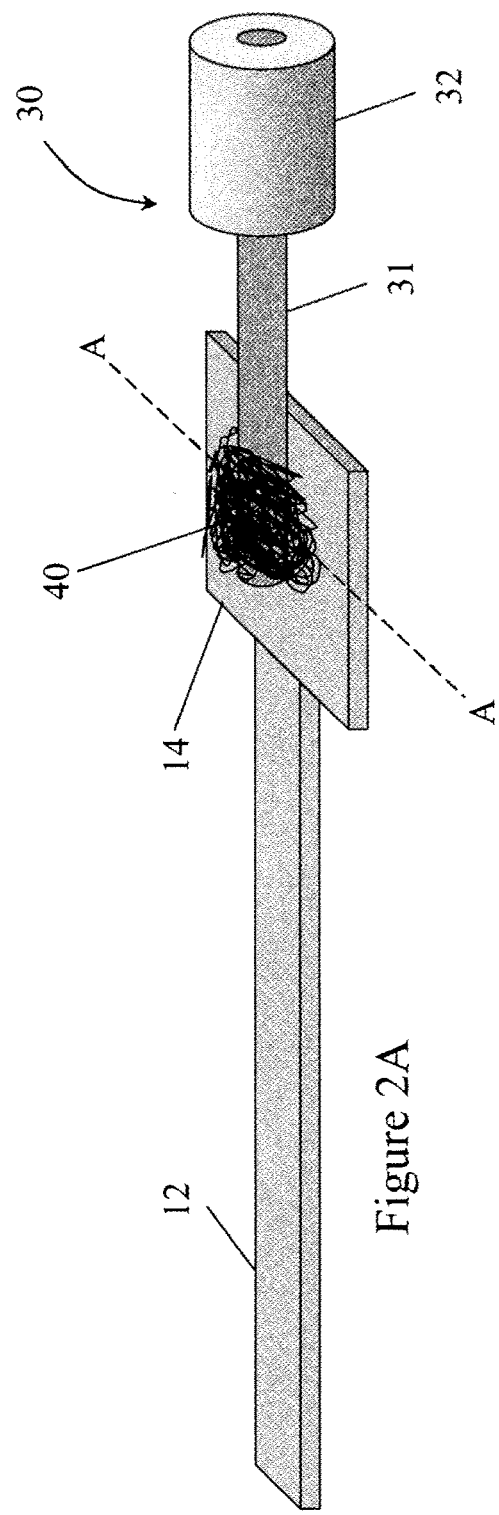
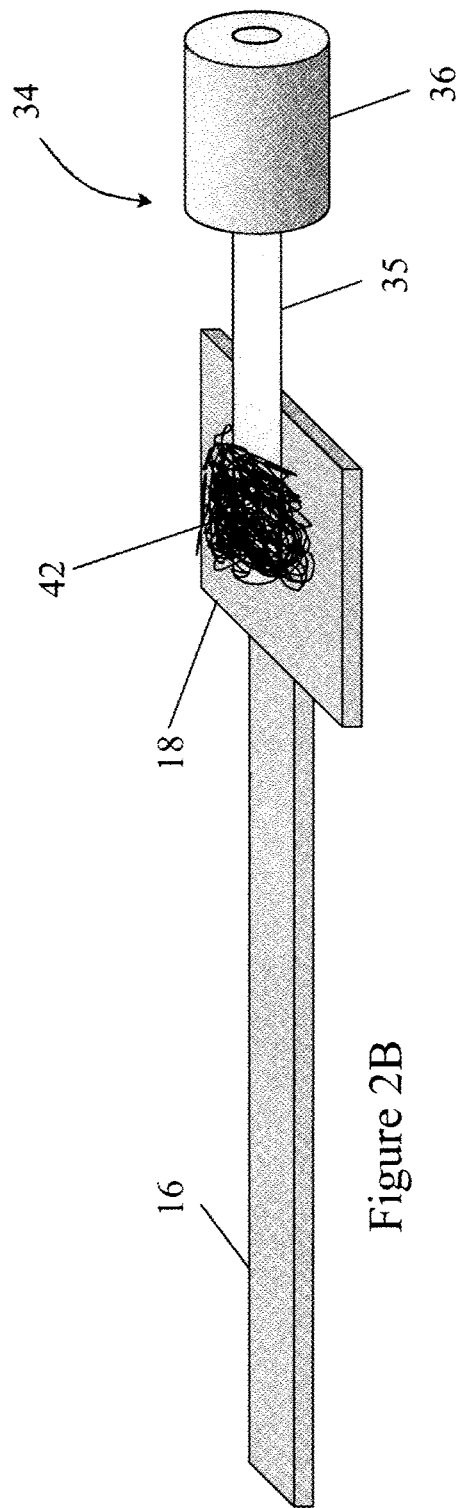
Figure 2A
Figure 2B

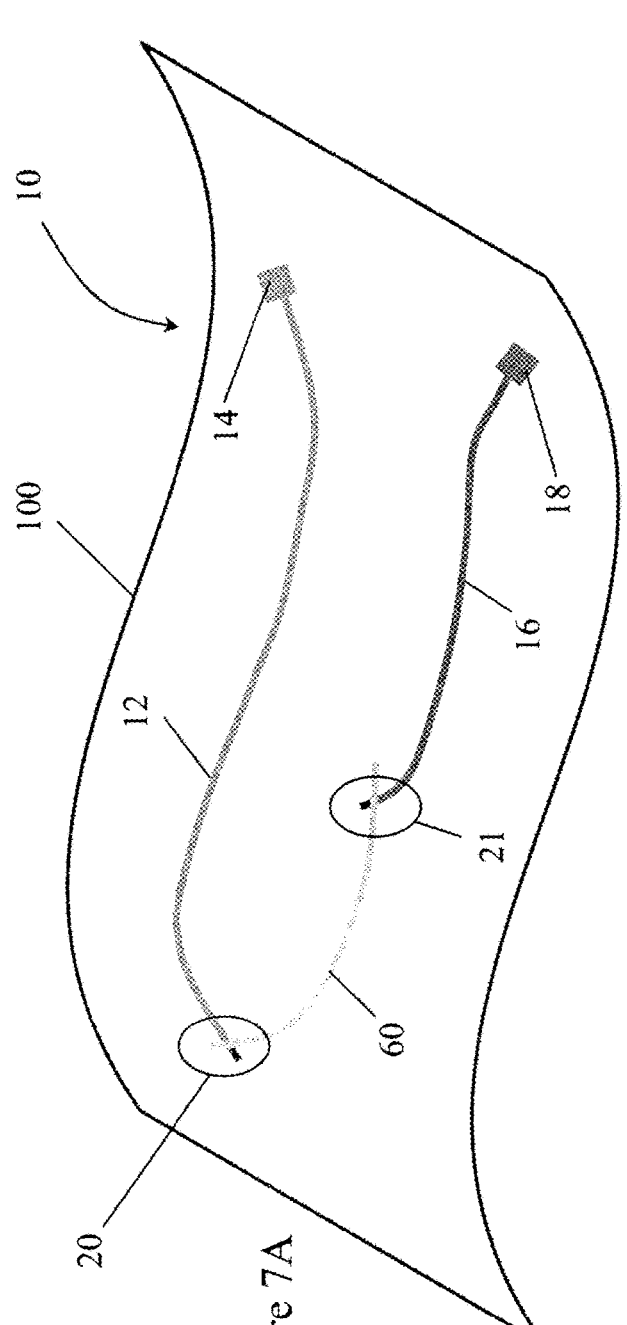
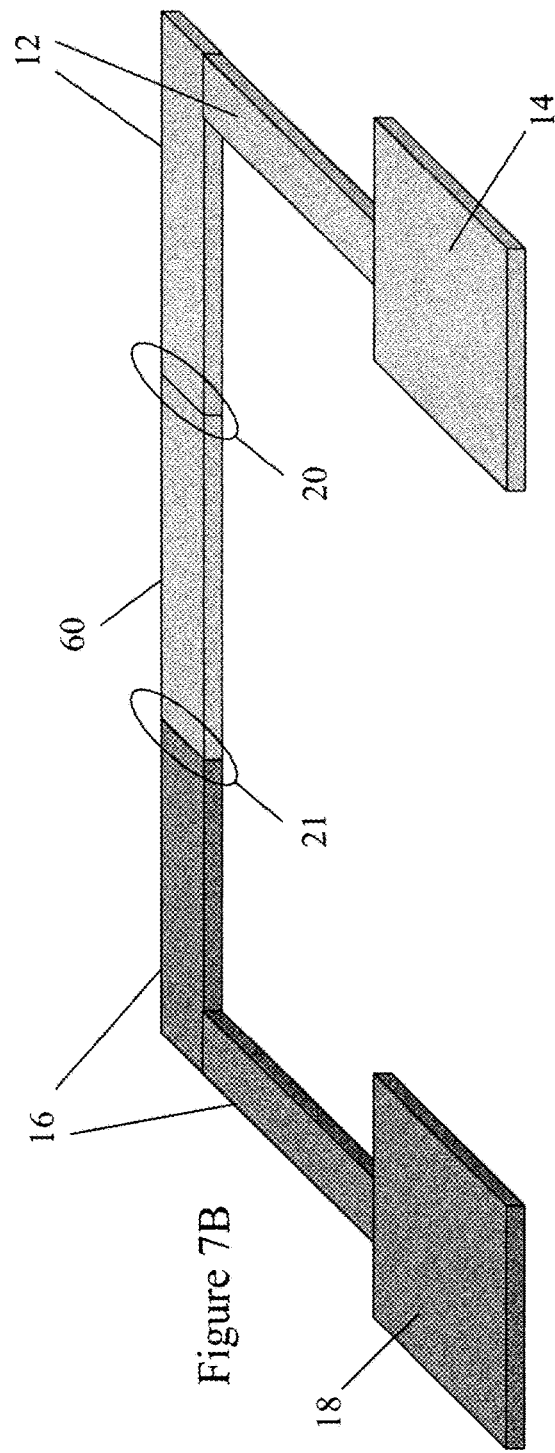
Figure 7A
Figure 7B

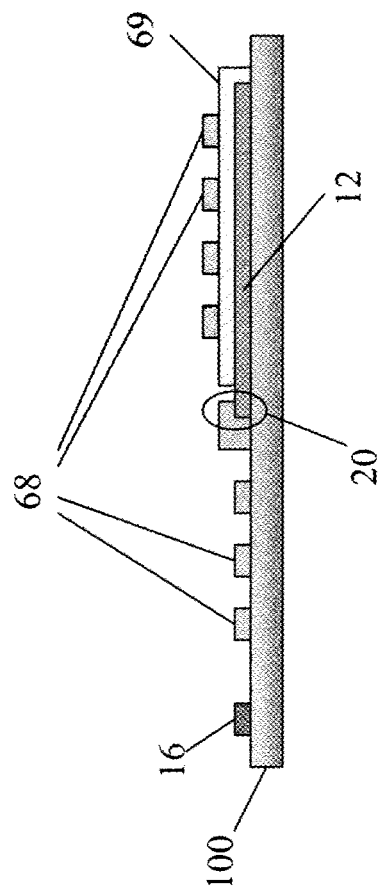
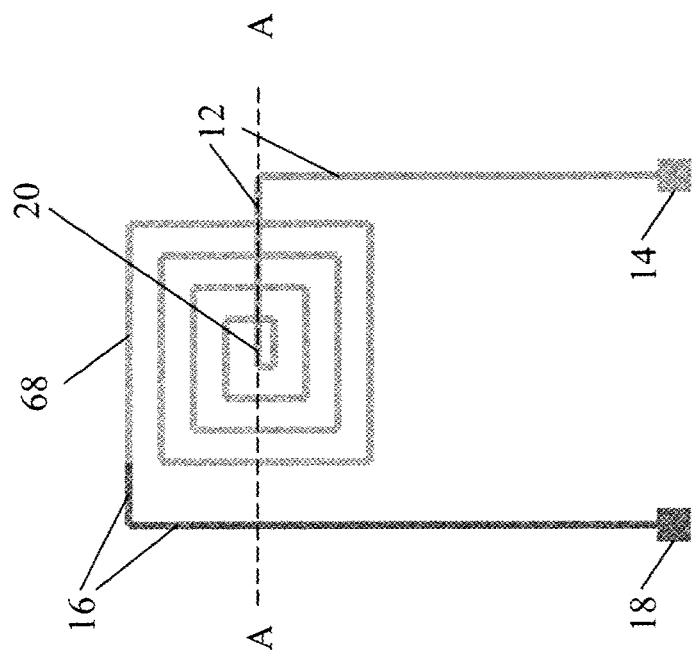
Figure 9A
Figure 9B

THERMOCOUPLE DEVICE

This application is a continuation of U.S. patent application Ser. No. 13/051,748, filed Mar. 18, 2011, which claims the benefit of U.S. Provisional Patent Application Ser. No. 61/315,534, filed Mar. 19, 2010, which is hereby incorporated by reference in its entirety.

FIELD OF THE INVENTION

The present invention is related to a printed thermocouple device and its uses.

BACKGROUND OF THE INVENTION

Common options for measuring temperature include the Resistance Temperature Detector (RTD), which has a metallic element possessing a positive temperature coefficient of resistance (decreasing resistance with increasing temperature), or a thermistor, which has a metal oxide element exhibiting a negative temperature coefficient (increasing resistance with increasing temperature). Unlike an RTD, thermocouples can achieve high accuracy without any restrictions on target immersion depth relative to the sensor diameter or length. Unlike a thermistor, thermocouples produce signals without any pronounced nonlinearity with temperature, thus allowing use over a greater temperature range. Finally, unlike a thermal colorimetric material, additional internal sensors are not necessary in order to obtain the signal. These factors make thermocouples particularly useful when used on medical devices, because they have superior capability for measuring temperature in a small or confined area. Accurate measurements of tissue or body fluids temperature are critically important during many medical procedures, but introduction of temperature measurement capability at a specific, controllable location during the procedure is often difficult and sometimes impossible. Application of a thermocouple device directly on a medical device solves this problem, removes uncertainty, during the procedure, about the exact location of the probe, and reduces the number of instruments that must be introduced or used during the medical procedure.

Thermocouples use two leads formed of dissimilar materials, for example one lead formed of constantan and the other formed of copper, that are joined at one end to form a thermocouple junction. The thermocouple junction produces a voltage, representative of the temperature, and that voltage varies as the thermocouple is exposed to various temperatures. Conventional thermocouples are often formed by joining together a pair of dissimilar metal wires, the metals having been chosen so that a voltage is observed depending on the size of the temperature difference between the joined and free ends of the pair.

Thermocouples can be used for both temperature measurement and temperature control by heating the thermocouple junction. The thermocouple effect is where a temperature differential can be converted directly into electrical energy, with the amount of electrical energy so generated providing a measurement of the temperature. The observed voltage then provides an estimate of the temperature differential along the length of the pair of wires according to standard equations well known to those of ordinary skill in the art.

Conversely, if a voltage is applied to a thermocouple, a temperature differential is created between the junction and the free ends of the two elements that comprise the thermocouple, with the junction being either cooled or heated depending on the direction of the applied DC current. If a number of such thermocouples are interconnected, a heating and cooling module (e.g., a Peltier module) may be constructed according to methods well known in the art. Several thermocouples that have been interconnected in series are often also commonly referred to as a thermopile.

As useful and versatile as modern thermocouples might be, they suffer from certain disadvantages, among which are that they are generally not suitable for use on flexible/irregular surfaces. Thermocouples are often made of thin wire pairs so that the device responds more quickly to temperature changes, but such a construction can make the thermocouple somewhat fragile. Several inventions have been aimed at demonstrating and solving the problems inherent in placing a temperature-measuring device directly on or in a medical device, but they have drawbacks and technical limitations.

For example, U.S. Patent Publication No. 2005/0257822 to Smith et al., describes printing finely powdered metals onto bedsheets and the like for use in medical scenarios. The metals are formulated into inks and deposited via silk screening. Silk screening is a popular printing method for applying lines to flexible objects. However, the objects must be held against a noncompliant backing during printing, such that silk screening is limited to two-dimensional or planar surfaces. Most medical devices of interest are polymeric, flexible, and three dimensional, rendering the silk screening approach problematic and often unusable. The silk screening method applies pressure to the substrate during the writing process.

U.S. Pat. No. 4,263,921 to Trugillo et al., describes a temperature sensitive endotracheal tube in which a thermistor is mounted to the tube. Mounting the thermistor rather than writing it directly on the tube surface leads to unwanted protrusion on the surface of the device which may prove damaging or uncomfortable upon introduction of the device to measure temperature during medical procedures. Further, there is an increased risk of the temperature sensor becoming loose and getting displaced during the procedure, leading to uncertainty in probe localization and subsequently in temperature monitoring. Another issue with the design is that thermistors, which rely on changes in resistance vs. temperature for a single metal, exhibit more non-linearity with temperature than do thermocouples, leading to measurement errors or the need for complicated correction algorithms during signal processing.

U.S. Pat. No. 4,046,139 to Horn describes a temperature sensor mounted on the cuff of an endotracheal tube, which could be a thermocouple, thermistor or color-sensitive material. A mounted thermocouple or thermistor would have the same drawbacks discussed above. Furthermore, a temperature sensor reliant on color change would be of limited usefulness when embedded in the body, because a method of sensing and transmitting the color, such as a camera or CCD, would also need to be introduced in able to detect real-time temperature changes.

U.S. Pat. No. 5,596,995 to Sherman et al., describes a thermocouple affixed to an end of a catheter. However, another thermocouple junction is formed where the leads are connected to dissimilar metals. Sherman describes a method for compensating for the unintentional second thermocouple formed at this connection. The electronics are formed separately from the device and then mounted to the device, leading to manufacturing challenges particularly if the catheter is very small in diameter; and also leading to the possibilities outlined above that the thermocouple junctions may be inadvertently displaced during the procedure. Like the other cases, a method is not provided that elegantly affixes the metals to the medical device.

Methods for applying metallic lines directly to flexible three-dimensional surfaces are very limited. Inkjet, or thermal transfer may be envisioned if appropriate substrate control and manipulation could be effected. Having rheological or thermal properties appropriate for precisely printing the ink formulations pose severe limitations. Another approach is silk screening on a flexible surfaces; however, it requires a backing material, such that printing on three dimensional objects is extremely difficult.

The present invention is directed to overcoming these and other deficiencies in the art.

SUMMARY OF THE INVENTION

In one aspect, the present invention relates to a thermocouple device comprising a flexible non-planar substrate, a first printed thermocouple element comprising a first metal containing ink composition applied to the flexible non-planar substrate, and a second printed thermocouple element in electrical contact with the first printed thermocouple element making a thermocouple junction. The second printed thermocouple element comprises a second metal containing ink composition with a Seebeck coefficient sufficiently different from the first metal containing ink composition for the first and second printed thermocouple elements to together produce a thermocouple effect.

In another aspect, the present invention relates to a heated thermocouple device comprising a flexible non-planar substrate, a first printed thermocouple element comprising a first metal containing ink composition applied to the flexible non-planar substrate and a second printed thermocouple element applied to the flexible non-planar substrate. The second printed thermocouple element comprises a second metal containing ink composition with a Seebeck coefficient sufficiently different from the first metal containing ink composition for the first and second printed thermocouple elements to together produce a thermocouple effect. The heated thermocouple device further comprises a heater element applied to the flexible non-planar substrate. The heater element comprises a third metal containing ink composition and is electrically connected to the first and second printed thermocouple elements.

Another aspect the present invention relates to a medical device comprising the thermocouple device of the present invention.

A further aspect of the present invention relates to a method of forming a thermocouple device. The method comprises applying a first metal containing ink composition to a flexible non-planar substrate, where the first metal containing ink composition forms a first printed thermocouple element and applying a second metal containing ink composition to the first metal containing ink composition applied to the flexible non-planar substrate where the second metal containing ink composition forms a second printed thermocouple element. The first and second metal containing ink compositions have a Seebeck coefficient sufficiently different from one another so that the first and second printed thermocouple elements together produce a thermocouple effect.

Thermocouples have been used as temperature sensors and have been incorporated in catheters for some time. However, these thermocouples have drawbacks and limitations as discussed supra. It is the intention of the present invention to provide multiple benefits over the present state of the art. The present invention produces temperature measuring devices that are more compact, more streamlined, less likely to cause trauma with contact to tissue, and less likely to dislodge, shift, or detach from the substrate. In those embodiments of the present invention where the thermocouple device provides functionalities in addition to temperature measurement, the present invention provides more closely coupled systems, reduced device count, more dense packing of devices, and reduced interconnection complexity.

BRIEF DESCRIPTION OF THE DRAWINGS

FIGS. 2A-B are perspective views of electrical connections that can be formed with contact pads of a thermocouple device.

FIGS. 7A-B show a schematic view of a heater thermocouple device that may be used as a heater. FIG. 7A shows the heater thermocouple device disposed on a non-planar medical device substrate. FIG. 7B shows a different configuration of the heater thermocouple device.

FIGS. 9A-B, respectively, show yet another embodiment of a thermocouple device of the present invention that may be used as a heater. FIG. 9A shows a top view of the thermocouple device where the heater element is configured, for example, in a coil. FIG. 9B shows a side cross-sectional view of the thermocouple device.

DETAILED DESCRIPTION OF THE INVENTION

In one aspect, the present invention relates to a thermocouple device comprising a flexible non-planar substrate, a first printed thermocouple element comprising a first metal containing ink composition applied to the flexible non-planar substrate, and a second printed thermocouple element in electrical contact with the first printed thermocouple element making a thermocouple junction. The second printed thermocouple element comprises a second metal containing ink composition with a Seebeck coefficient sufficiently different from the first metal containing ink composition for the first and second printed thermocouple elements to together produce a thermocouple effect.

For example, the thermocouple devices of the present invention can be used as temperature sensors and comprise a thermocouple having elongated ends joined together at their distal ends to form the thermocouple and their proximal ends connected to a connector mounted in the catheter. External equipment may be connected to the connector of the catheter to receive the temperature signals of the thermocouple for signal processing to determine the temperature sensed. The thermocouple is typically disposed at the distal end of the catheter.

The present invention provides a temperature measurement device printed directly to a three dimensional surface, for example a medical device, without the disadvantages noted supra.

Figure 1:
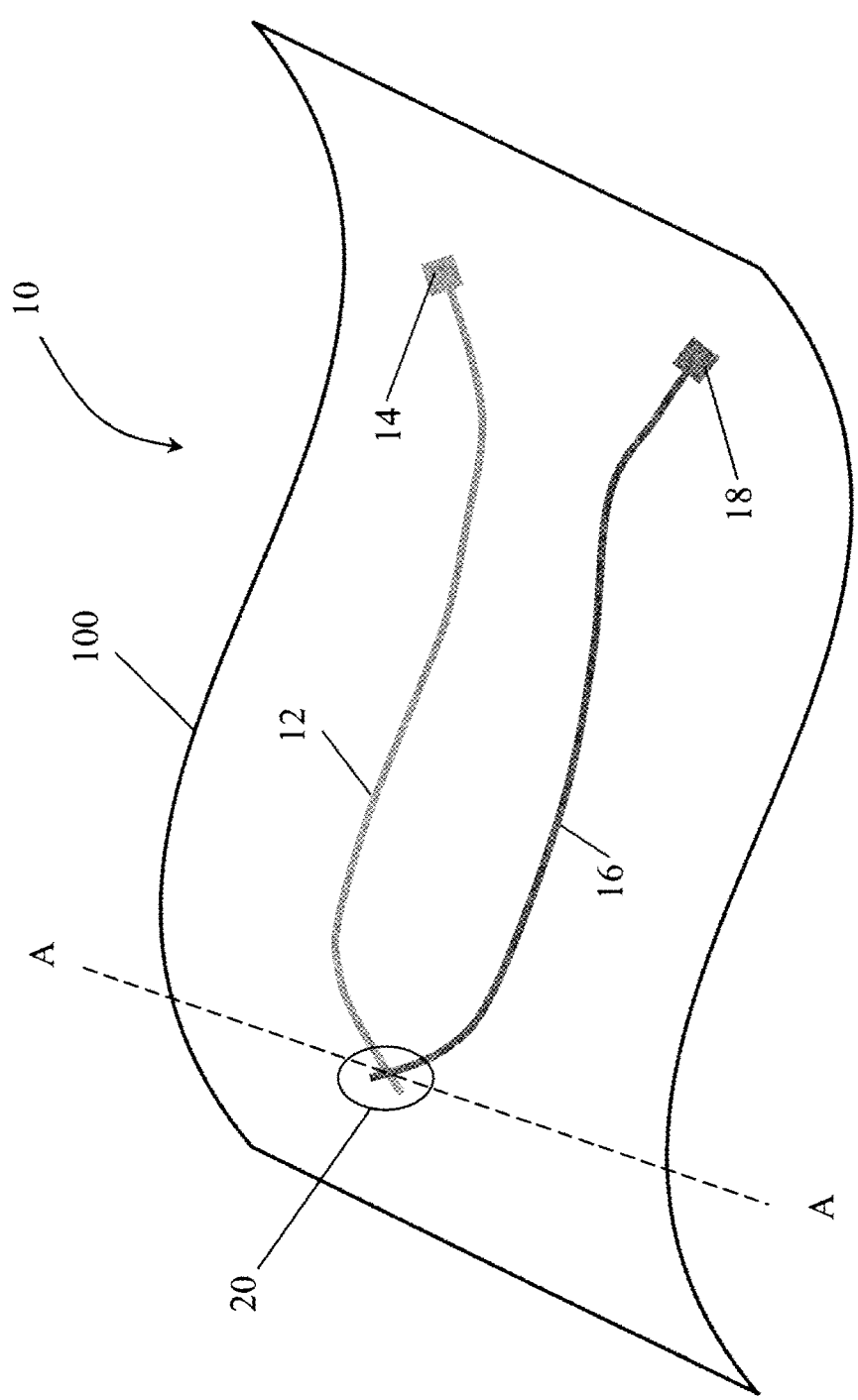
FIG. 1 shows a tilted view of an example of a thermocouple device of the present invention disposed on a non-planar medical device substrate.

Referring now to the drawings and particularly to FIG. 1, the thermocouple device 10 includes a first printed thermocouple element 12 connected to a first contact pad 14 using a first metal-containing ink composition. A second printed thermocouple element 16 connected to a second contact pad 18 are formed using a second metal-containing ink composition such that the thermocouple elements 12 and 16 contact each other and form a thermocouple junction 20. The first and second metal-containing ink compositions are chosen such that the thermoelectric EMF formed at thermocouple junction 20 due to the Seebeck effect is of a useful magnitude.

The thermocouple device 10 is disposed on substrate 100. In the present invention, the substrate 100 includes any non-planar or "three dimensional" medical device which could be, for example, a medical device. The non-planar substrate could be, for example, a cylindrical object, a spherical object, a wire, a catheter, a fabric, a multi-branching substantially tubular device, or a flexible non-planar substrate which may distort upon application of force. The substrate 100 could be polymeric, ceramic, metallic, or a combination thereof. In addition, the substrate 100 could have elastic properties ranging from highly flexible to extremely rigid. Many of the aspects of the present invention are particularly well suited for the formation of thermocouple devices on flexible, polymeric medical devices. However, the present invention is not intended to be limited by either the materials of construction or the elastic properties of the substrate 100.

In one embodiment, the thermocouple device of the present invention is printed on a flexible non-planar substrate which has an irregular surface. An irregular surface is a surface lacking uniformity or symmetry, having an uneven shape, position, or arrangement. For example, an irregular surface could be a surface that has indentations or jagged edges.

In another embodiment, the thermocouple device of the present invention further comprises electrical connectors electrically coupled to the first and the second printed thermocouple elements. Depending on the design of the thermocouple device these electrical connectors could also be connected to multiple printed elements at multiple locations using the techniques described in the present invention. A person of skill in the art can readily configure the electrical connectors to be suitably connected for different configurations of the thermocouple device.

Figure 13:
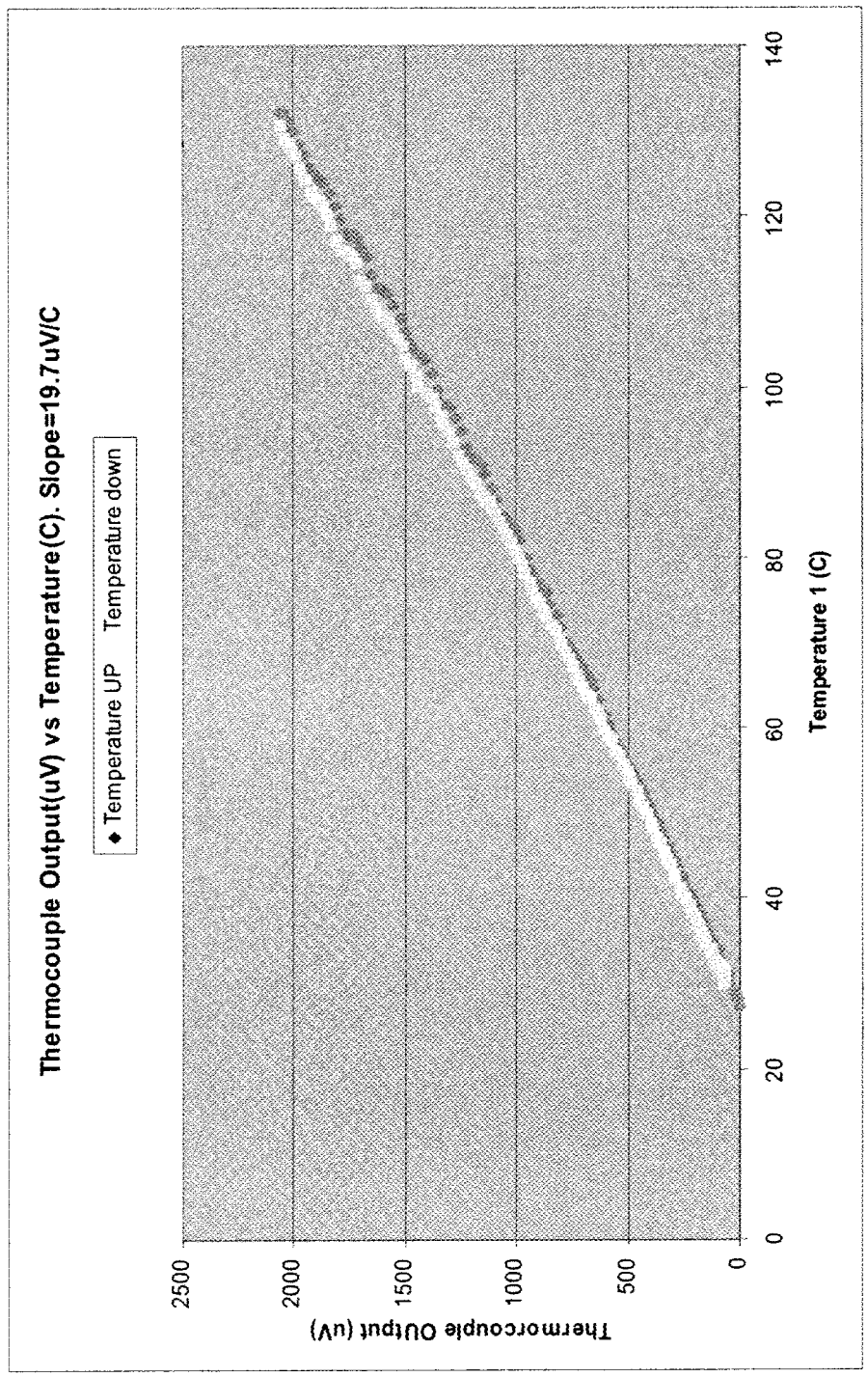
FIG. 13 is a graph showing experimental temperature readings from a thermocouple device of the present invention as a function of time where the ambient temperature is programmed to fluctuate.

In another embodiment, the thermocouple device of the present invention can comprise a voltage reader operably coupled to the electrical connectors to measure the voltage between the first and second printed thermocouple elements. The voltage is generated due to the temperature differential between the first and the second printed thermocouple elements. This voltage can be calibrated to temperature to provide a direct readout of the temperature. Alternatively, standardized data sets could be provided to convert the voltage reading to temperature (see for example, FIG. 13).

In yet another embodiment, the electrical connectors could also be coupled to a voltage source which can be used to apply current to the first and the second printed thermocouple elements, thereby providing heating or cooling to the thermocouple junction.

In another embodiment, the thermocouple device of the present invention comprises an overcoat layer covering the first and second printed thermocouple elements. The surface or substrate materials used to print the thermocouples may be non-conducting or coated with a non-conducting layer(s).

In another embodiment, the thermocouple device of the present invention comprises an intermediate layer positioned between the flexible non-planar substrate and the first and second printed thermocouple elements. The intermediate layer could function in many ways, such as a sealing layer, insulating layer, adhesive layer, structural support layer, or a combination thereof.

Many polymeric materials known in the art can be used to make the substrates, overcoat layers, and intermediate layers of the present invention. Non-limiting examples of polymeric materials that may be used to manufacture these aspects of the present invention include epoxy, polyacrylate, silicone or natural rubber, polyester, polyethylene napthalate, polypropylene, polycarbonate, polystyrene, polyvinyl fluoride ethyl-vinyl acetate, ethylene acrylic acid, acetyl polymer, poly(vinyl chloride), silicone, polyurethane, polyisoprene, styrene-butadiene, acrylonitrile-butadiene-styrene, polyethylene, polyamide, polyether-amide, polyimide, polyetherimide, polyetheretherketone, polyvinylidene chloride, polyvinylidene fluoride, polycarbonate, polysulfone, polytetrafuoroethylene, polyethylene terephthalate, polyhydroxyalkanoate, poly(p-xylylene), liquid crystal polymer, polymethylmethacrylate, polyhydroxyethylmethacrylate, polylactic acid, polyhydroxyvalerate, polyvinyl chloride, polyphosphazene, poly(ε-caprolactone). Copolymers or mixtures of polymers may also be used for the purposes of the present invention.

The first and the second metal containing ink compositions of the present invention independently comprise a metal powder selected from the group consisting of copper, palladium, chromel, alumel, rhenium, nickel-chromium-silicon, constantan, cadmium, aluminum, platinum, rhodium, iridium, molybdenum, tantalum, beryllium, zinc, tin, chromium, nickel, nickel-chromium, nickel-aluminum, nickel-silicon, iron, tungsten, lead, silver, gold, magnesium, silicon or alloys thereof.

The thermocouple junction and leads may be formed from any two metals exhibiting sufficiently different Seebeck coefficients. The Seebeck coefficient typically varies with temperature, so selection of metal pairs should also minimize any nonlinearities in the difference over the temperature range of interest. Range and accuracy of measurement may be affected by choice of materials, and many standard metal pairs have been identified and are commonly used as thermocouples. For example, a copper-constantan junction defines a T-type thermocouple; while a combination of platinum and a platinum-rhodium alloy yields a Type R or Type S thermocouple, depending on the rhodium content in the alloy. Other common thermocouple metal pairs include chromel-constantan (Type E); iron-constantan (Type J); chromel-alumel (Type K); and nicrosil-nisil (Type N). Many non-standard thermocouples can also be envisioned, such as silver-nickel, copper-nickel, tungsten-nickel, gold-palladium, etc. Semiconductor materials also make excellent thermocouples; however it is difficult to obtain connection wires made of such materials so they are normally only useful for solid-state applications where interconnects are not required. With respect to ready availability of ink materials and a clearly detectable reproducible temperature signal, silver-nickel or tungsten-nickel are most preferred.

Additives and fillers are often present in the polymer matrices of the present invention in order to improve mechanical properties, enable processing, and add radiopacity to the devices. The surface of the polymer may be further modified to enhance biocompatibility or to alter frictional or adhesive properties through application of: additional polymeric, oligomeric, or surfactant coating layers; mechanical or chemical etching; or plasma, corona, or flame treatment.

In one embodiment of the thermocouple device of the present invention, the first, second or other metal containing ink compositions independently comprise a binder selected from the group consisting of poly(vinyl chloride), silicone, polyurethane, polyisoprene, styrene-butadiene, acrylonitrile-butadiene-styrene, polyethylene, polyamide, polyether-amide, polyimide, polyetherimide, polyetheretherketone, polyvinylidene chloride, polyvinylidene fluoride, polycarbonate, polysulfone, polyethylene, polytetrafluoroethylene, polyethylene terephthalate, polyhydroxyalkanoate, poly(p-xylylene), liquid crystal polymer, polymethylmethacrylate, polyhydroxyethylmethacrylate, polylactide, polyglycolide, polyisoprene, polycaprolactone, cyanoacrylates, polyvinyl butyral, polyvinyl formal, polyethylene oxide, polyvinyl alcohol, polyvinylpyrrolidone, cellulose esters, cellulose ethers, carrageenan, gelatin, chitosan, and combinations or copolymers thereof. Blends of such polymers can be especially helpful in optimizing mechanical and adhesive properties. They may also play a role in providing a reliable dispersion of the metal particles, or in adjusting the rheological characteristics of the ink.

In order to ensure good adhesion to the polymeric substrate and adequate mechanical properties of the printed trace itself, the ink or paste should comprise a polymeric binder combined with a sufficient level of metallic particles to afford contiguous contact of the particles in the dry form. The polymeric binder may be selected from any of the commonly available thermoplastic or thermoset polymers, or combinations thereof, in order to yield the most optimal properties. The polymer may be dissolved or dispersed in an organic solvent which also may play a role in enhancing adhesion to the substrate device. Additives may be present in the ink or paste, including but not limited to crosslinkers, catalysts, inhibitors, dispersants, surfactants, thickeners, matting agents, and the like as required to optimize both the manufacturing process and the properties of the final product. For a silicone medical device, for example, the optimal binder polymer may comprise polydimethylsiloxane, along with appropriate crosslinking chemistry to yield a sufficiently robust matrix for the metal particles. For a poly(vinyl chloride) substrate medical device, an optimal binder polymer for the printing ink may be poly(vinyl chloride) dissolved in a solvent which slightly swells the substrate to allow entanglement of the ink polymer and the substrate polymer, leading to optimal adhesion.

Solvents which may be used in the present invention include, without limitation: any liquid capable of dissolving or dispersing the ink binder polymer, such as paraffinic hydrocarbons such as cyclohexane; aromatic hydrocarbons such as toluene or xylene; halohydrocarbons such as methylene dichloride; ethers such as anisole or tetrahydrofuran; ketones such as acetone, methyl ethyl ketone or methyl isobutyl ketone; aldehydes; esters such as ethyl carbonate, 4-butyrolactone, 2-ethoxyethy acetate or ethyl cinnamate; nitrogen-containing compounds such as n-methyl-2-pyrrolidone or dimethylformamide; sulfur-containing compounds such as dimethyl sulfoxide; acid halides and anhydrides; alcohols such as ethylene glycol monobutyl ether, a-terpineol, ethanol, or isopropanol; polyhydric alcohols such as glycerol or ethylene glycol; phenols; or water or mixtures thereof. The binder polymer may also be present as an undissolved dispersion, or polymer latex, suspended in water.

Preferred solvents are those which have the lowest toxic potential when left behind in residual quantities, such as acetone, 1-butanol, ethanol, 1-propanol, methyl acetate, anisole, methyl acetate, methyl ethyl ketone, and the like. Combinations of solvents sometimes prove especially useful in obtaining good solubility with minimal risk of toxicity. It is preferable to choose solvents which evaporate at a rate such that the temperature of the polymeric substrate can be maintained below its softening point, so that the device is not damaged as the solvent is driven off.

Referring to FIG. 2A, electrical connection of thermocouple device 10 to other modules used, for example, to detect or supply power can be accomplished in many ways. In one preferred embodiment a first interconnection assembly 30, consisting of a first conductor 31 surrounded by a first insulator 32, communicates electrically with the first contact pad 14 through a first bonding material 40. As shown in similar fashion in FIG. 2B, a second interconnection assembly 34, consisting of a second conductor 35 surrounded by a second insulator 36, communicates electrically with the second contact pad 18 through a second bonding material 42. In order to prevent the creation of secondary thermocouple junctions, first contact pad 14, first conductor 31, and first bonding material 40 must be constructed of the same metal or metal alloy. Similarly, second contact pad 18, second conductor 35, and second bonding material 42 must also be constructed of the same metal or metal alloy. In one preferred embodiment, the bonding materials 40 and 42 are epoxy adhesives filled with the appropriate metal or metal alloy flakes or powders. An example of a preferred silver-containing epoxy is Epo-Tek® H20E sold by Epoxy Technology, Inc® (Billerica, Mass.). In another preferred embodiment, the bonding materials 40 and 42 are the printed thermocouple element inks themselves. An example of a preferred nickel-containing ink is 116-25 sold by Creative Materials, Inc. (Tyngsboro, Mass.). Alternative methods of creating connections to thermocouple device 10 include ultrasonic bonding, swaging, screw terminals, pressure contacts, soldering, and brazing.

The thermocouple device of the present invention may comprise first and second printed thermocouple elements which collectively have a thickness of 0.1 to 500 microns. In another embodiment, the thermocouple device could be such that the first and second printed thermocouple elements collectively have a thickness of 12 to 80 microns In another embodiment the thermocouple device of the present invention can comprise a plurality of thermocouple junctions formed by a combination of a plurality of printed thermocouple elements. A plurality of thermocouple junctions may be used to increase the area over which temperature measurements are taken. Also, the multiple printed thermocouple elements can be utilized to create multiple thermocouple junctions disposed at specific locations on a medical device. This allows the gathering of temperature information over a region of the medical device rather than at a single point.

Figure 3:
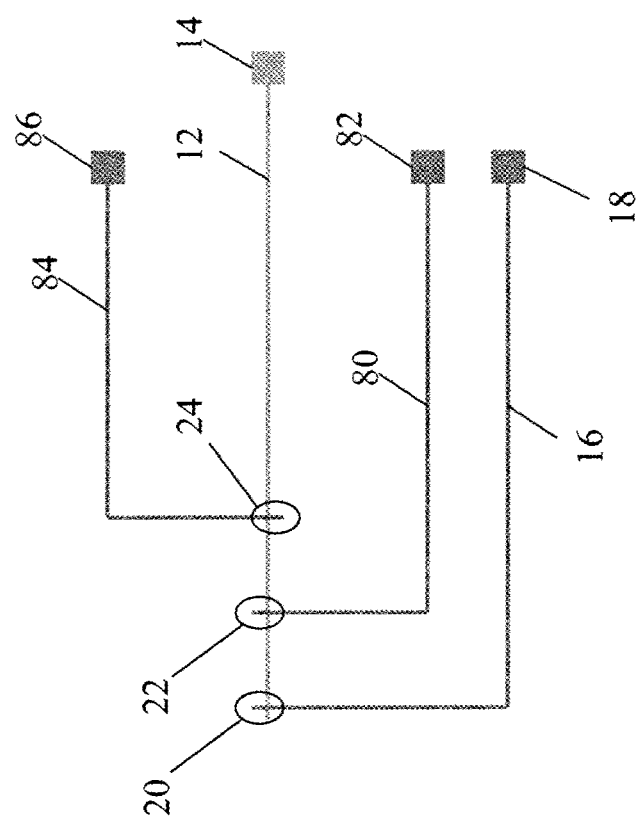
FIG. 3 is a schematic showing an example of a plurality of thermocouple junctions that can be suitably configured to create multiple thermocouple junctions at different locations on a medical device.

Referring to FIG. 3, in one embodiment, a second thermocouple junction 22 can be produced by providing a third contact pad 82 connected to a third printed thermocouple element 80 which in turn comes in contact with the first printed thermocouple element 12. In similar fashion a fourth printed thermocouple element 84 connected to a fourth contact pad 86 can be utilized to create a third thermocouple junction 24. The multiple thermocouple junctions can be precisely located across the medical device substrate to provide temperature measurements over an area rather than at a single point. As will be obvious to those of skill in the art, the positions of the thermocouple junctions, the materials used to form the printed thermocouple elements, and the electrical topology of the junctions can all be varied for the needs of a particular application. All combinations thereof are within the scope of the present invention.

The thermocouple device of the present invention can be disposed on, for example, a substantially cylindrical medical device substrate such that a significant portion of the thermocouple device forms a solenoidal electrical coil that can be used to deliver or sense electromagnetic fields and energy. By providing switching and timing circuitry the thermocouple device can alternatively be read as a temperature sensor and energized to provide localized radio-frequency heating.

Figure 4:
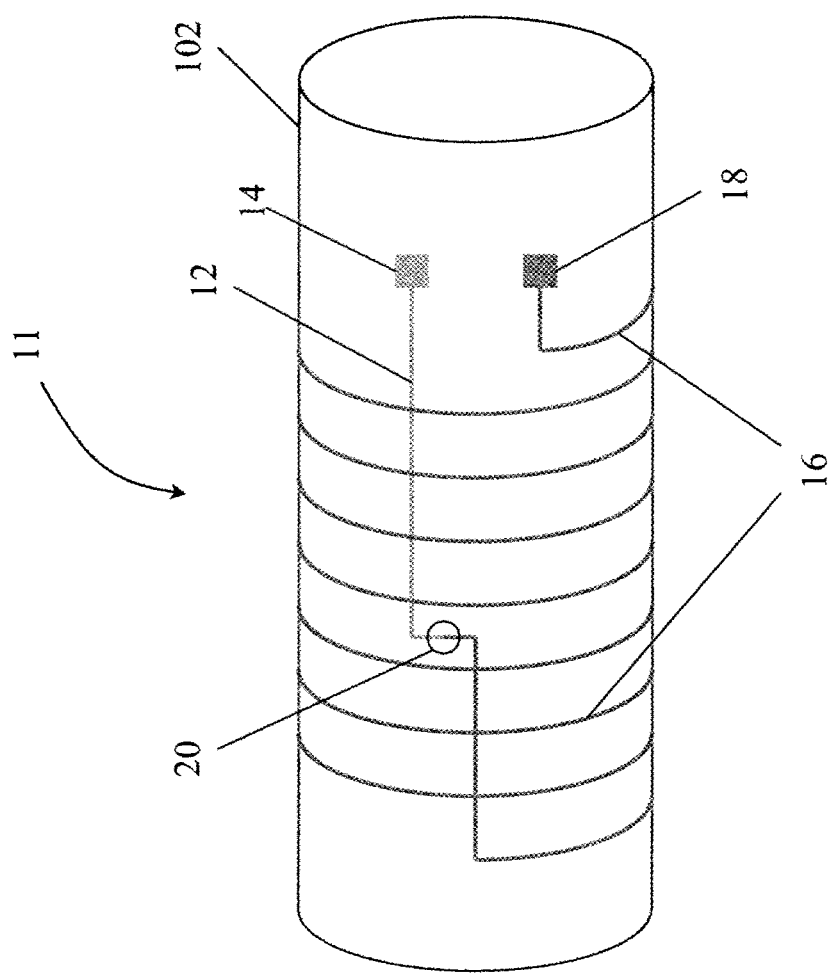
FIG. 4 shows a perspective view of a thermocouple device that can also be used as a radio-frequency (RF) coil. For example, as shown in this figure the thermocouple device could be printed on a suitable cylindrical substrate in the form of a spiral which could be used as radio-frequency transmitter, radio-frequency receiver or a transceiver.

In another embodiment, the thermocouple device of the present invention can further comprise a voltage reader operably coupled to the electrical connectors to measure the voltage between the first and/or second printed thermocouple elements and a radio frequency module operably coupled to the electrical connectors of the first and/or second printed thermocouple elements to generate radio frequency waves or to detect radio frequency waves. Referring now to FIG. 4, a substantially cylindrical thermocouple device 11 can be formed on a substantially cylindrical medical device substrate 102. "Substantially cylindrical" means that at least a portion of the medical device substrate is closed and sufficiently well-behaved to permit the printing of one or more coils or loops. The actual cross-section of the medical device substrate is ideally circular, but may also be elliptical, polygonal, or an arbitrary shape. The cross-section may also vary with axial position. In a preferred embodiment, the substantially cylindrical thermocouple device 11 is disposed such that it forms in part a multi-loop solenoid coil which can sense or transmit electromagnetic fields and energy.

In one embodiment, thermocouple device of the present invention comprises the radio-frequency module which can be, for example, a radio frequency generator, radio frequency detector, or a combination thereof.

Figure 5:
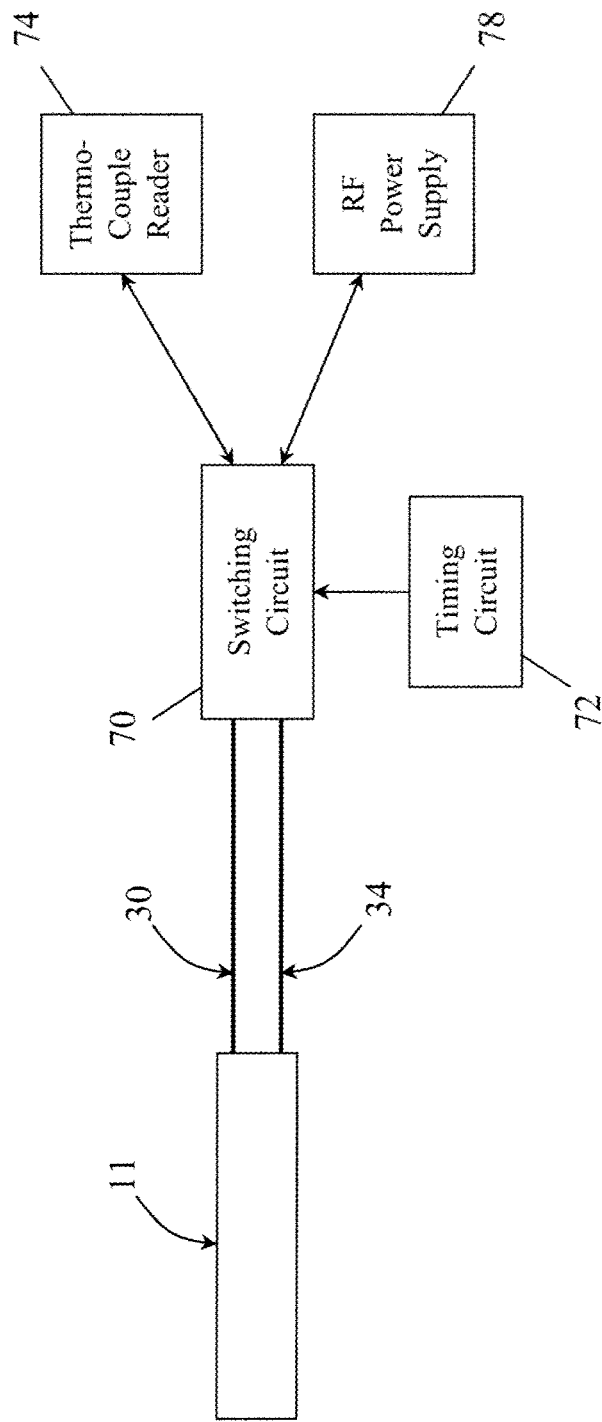
FIG. 5 is a schematic of the control elements that allow a thermocouple device to act as a radio-frequency coil. For example, as shown here, the control elements include a thermocouple reader which could be used to provide a read out of the temperature detected by the thermocouple. Another control element which may be coupled to the thermocouple device is shown as RF power supply. This power supply could be used, for example, to generate RF in the thermocouple. The RF power supply could be readily replaced with a RF detector to monitor or detect RF. An optional control element is shown as the switching circuit. This switching circuit could be functionally coupled to a timing circuit that allows for suitably timing the switching circuit. The switching circuit allows for switching the coupling of the thermocouple reader and the RF power supply to the thermocouple element.

In yet another embodiment, the thermocouple device of the present invention further comprises a switching module which selectively couples the electrical connectors of the first and/or second printed thermocouple elements to the voltage reader or the radio frequency module. Referring to FIG. 5, the substantially cylindrical thermocouple device 11 can be made to function as both a temperature sensor and either a sensor or transmitter of electromagnetic fields and energy by connecting the first and second interconnection assemblies 30 and 34 to a switching circuit 70 which alternately connects the device to a thermocouple reader 74 to take temperature measurements or to, in one preferred embodiment, a RF power supply 78 to excite the solenoid coil in the substantially cylindrical thermocouple device 11 in order to couple electromagnetic fields and/or energy into body tissue. A timing circuit 72 is utilized to control the switching circuit 70. In one preferred embodiment, the scheme of FIG. 5 would be used to ablate tissue and monitor the local temperature in order to control the procedure. It should be noted that the flat coil and the solenoid coil differ primarily in geometry and are equally able to be employed and controlled by the scheme of FIG. 5.

Figure 6:
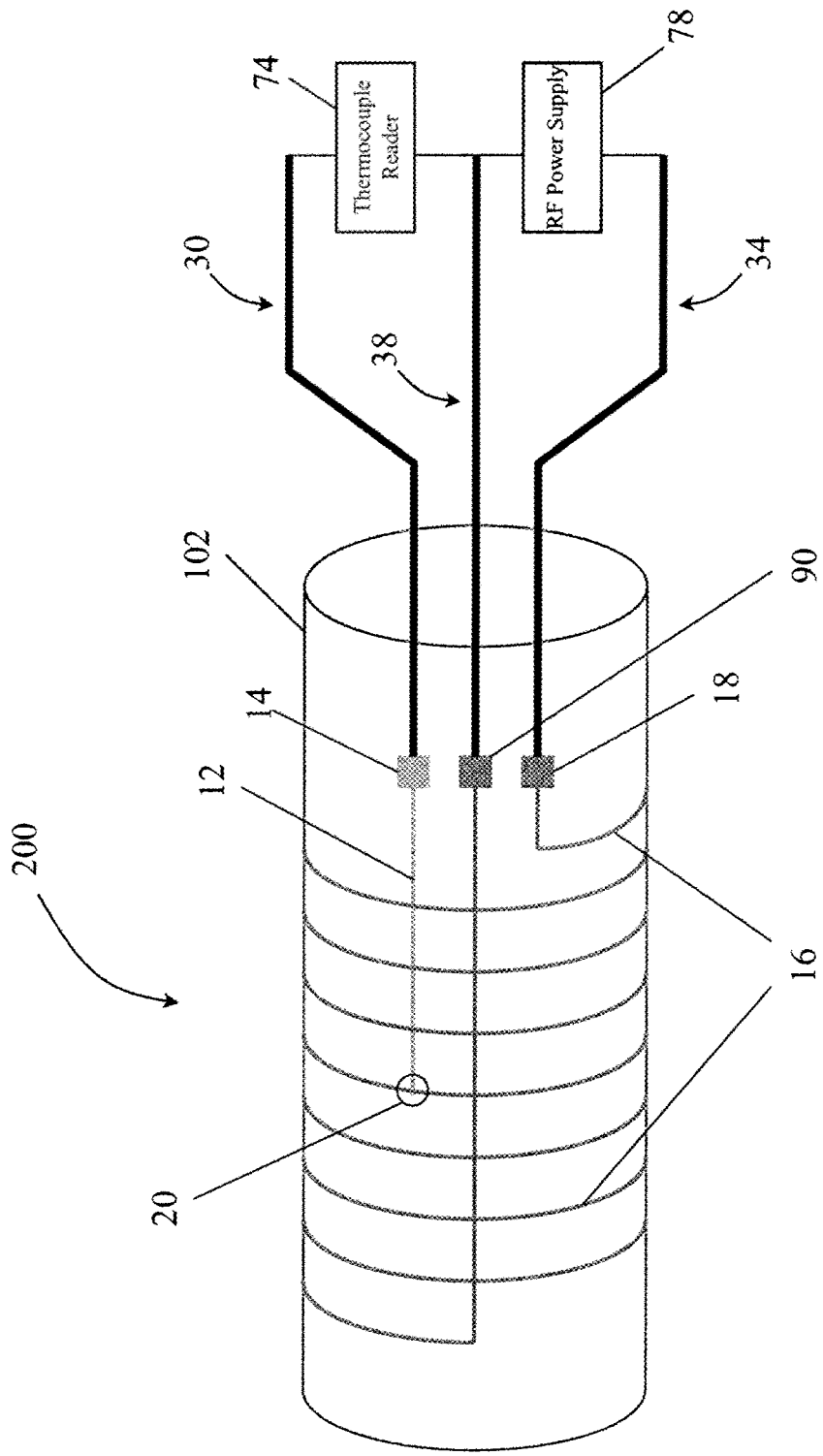
FIG. 6 is a schematic view showing an example of a thermocouple device that functions simultaneously and continuously as a thermocouple and a radio-frequency coil. The circuits connected to the device can be configured such that both the radio-frequency coils and the thermocouple reader are continuously functioning to read the temperature and generate radio-frequency. The RF power supply can also be replaced with a RF detector to continuously monitor and detect RF.

In another embodiment, the thermocouple device of the present invention can have the electrical connectors of the first and/or second printed thermocouple elements permanently connected to the voltage reader and the radio frequency module. Referring now to FIG. 6, an alternative preferred embodiment of the substantially cylindrical thermocouple device 11 of FIG. 4 is depicted. A three-terminal thermocouple device 200 is constructed by forming the second printed thermocouple element 16 into a multi-turn solenoid coil and terminating it at a common lead contact pad 90. The thermocouple junction 20 is formed by contacting the first printed thermocouple element 14 to one of the coils. A third interconnection assembly 38 communicates electrically with the common lead contact pad 90. As in previous embodiments, the thermocouple reader 74 is used to produce temperature measurements. However, in the present embodiment, the thermocouple reader is connected between the first and third interconnection assemblies 30 and 38. Also similar to previous embodiments, the RF power supply 78 is used to provide RF energy. However, in the present embodiment the RF power supply is connected between the second and third interconnection assemblies 34 and 38. The advantage of the present embodiment is that temperature measurements and RF excitation can occur continuously and simultaneously. No switching or timing circuits are required, and the three-terminal thermocouple device 200 does not alternate between measurement and excitation.

The three-terminal thermocouple device permits simultaneous and continuous temperature measurements while a specific section of the thermocouple device is utilized as, for example, a heater, a RF heater, or an electromagnetic field sensor. This arrangement reduces terminal count and reduces the complexity of interconnection.

In another aspect, the present invention relates to a heated thermocouple device comprising a flexible non-planar substrate, a first printed thermocouple element comprising a first metal containing ink composition applied to the flexible non-planar substrate and a second printed thermocouple element applied to the flexible non-planar substrate. The second printed thermocouple element comprises a second metal containing ink composition with a Seebeck coefficient sufficiently different from the first metal containing ink composition for the first and second printed thermocouple elements to together produce a thermocouple effect. The heated thermocouple device further comprises a heater element applied to the flexible non-planar substrate. The heater element comprises a third metal containing ink composition and is electrically connected to the first and second printed thermocouple elements.

For example, the geometry and electrical properties of the metallic elements that make up the thermocouple device can be adjusted to create a section of the device that possesses a large portion of the overall series resistance of the device. This section then acts as a heater element that delivers localized energy when the thermocouple device is actively driven with a power supply.

In another embodiment, the heated thermocouple device of the present invention further comprises electrical connectors electrically coupled to the first and the second printed thermocouple elements. A person of skill in the art can readily configure the electrical connectors to be suitable for different configurations of the heated thermocouple device. Depending on the design of the thermocouple device, these electrical connectors could be connected to multiple printed elements at multiple locations using the techniques described in the present invention. Depending upon the design of the device, the electrical connectors can also be independently attached to the heater element of the heated thermocouple element.

Referring to FIG. 7A, the thermocouple device can alternatively be viewed as a three-section device where a heater element 60 is specifically identified and communicates electrically with the second printed thermocouple element 16 through a heater element connection 21. Heater element 60 is constructed of the same metal or metal alloy as the second printed thermocouple element 16 and, consequently, the thermocouple junction 20 is formed at the interface between heater element 60 and the first printed thermocouple element 12.

Referring to FIG. 7B, the device of FIG. 7A is shown in a perspective view to aid understanding of other, subsequently-described embodiments of the present invention. Of particular note, heater element 60 can be specifically designed to be highly resistive relative to the first and second printed thermocouple elements 12 and 16 so that when the thermocouple device 10 is electrically excited most of the Joule heating in the device is confined to heater element 60.

Figure 8A:
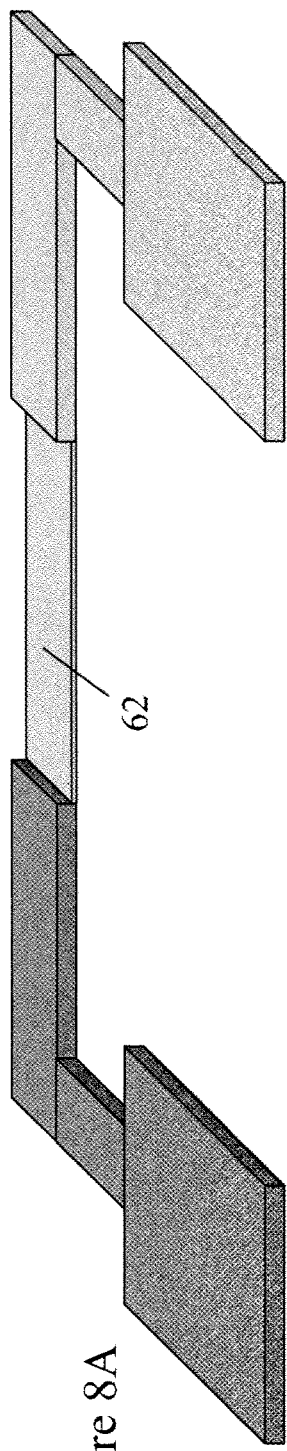
FIGS. 8A-C show perspective views of various embodiments of a thermocouple device that may also be used as a heater. The dimensions of the heater element can be easily configured according to the heating requirements and the use of the heating element.
Figure 8B:
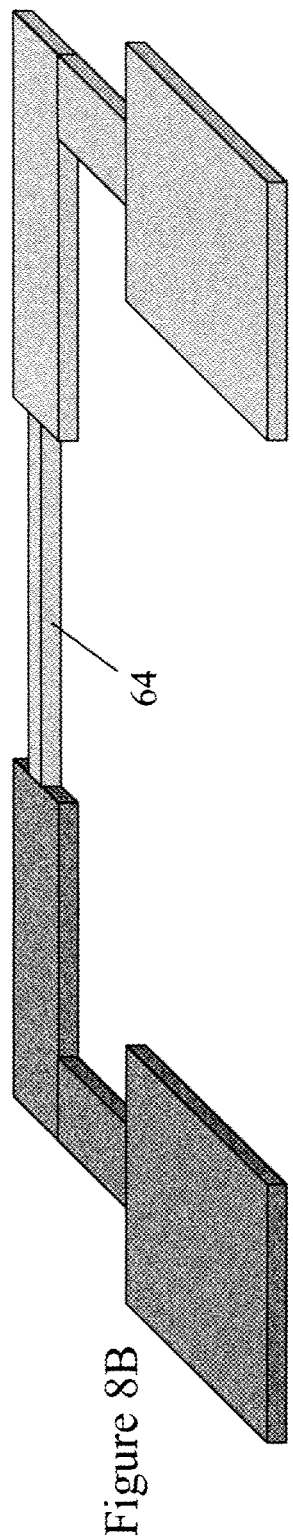
Figure 8C:
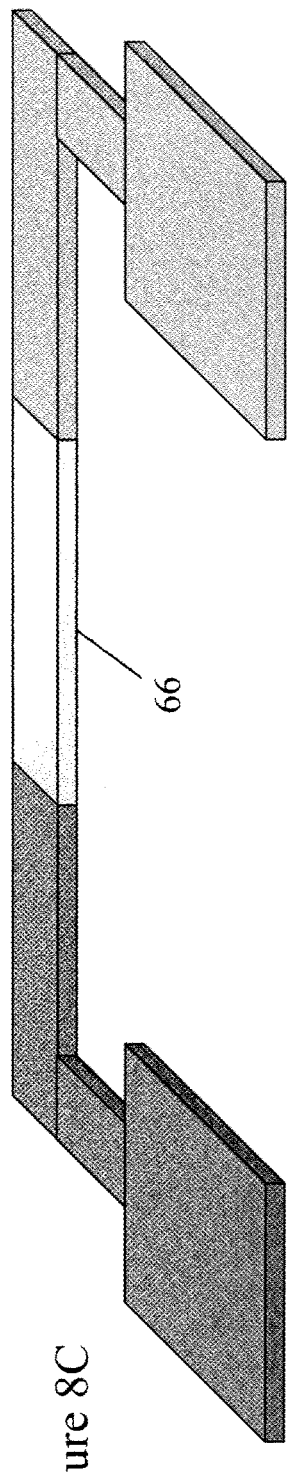

Referring to FIGS. 8A-C, there are multiple approaches to designing heater element 60. As shown in FIG. 8A, a heater element based on trace thickness 62 can be formed by reducing the thickness of the printed trace. As shown in FIG. 8B, a heater element based on trace width 64 can be formed by reducing the width of the printed trace. As shown in FIG. 8C, a heater element based on material formulation 66 can be formed by increasing the bulk resistivity of the trace by, for example, reducing the concentration of the metal or metal alloy filler in the ink. It should be noted that, depending on the printing methodology employed, the fabrication of the heater element may require a printing step separate from that employed to produce the second printed thermocouple element 16.

Referring to FIG. 9A, a fourth approach according to the present invention is to create a heater element based on trace length 68. Geometrically, the heater element could be disposed as a single line, a serpentine, an irregular polygon, or some other shape. In one particular embodiment, the coil, is shown explicitly in FIG. 9A and is especially preferred for two reasons. First, the coil geometry allows the heater element to be designed for precise delivery of heat over a large area. Second, as will be noted again below, the coil structure provides the thermocouple device with an electrical inductor which may be used to either sense or transmit electromagnetic fields and energy. The coil geometry does involve at least one added fabrication step. As shown in FIG. 9B, an interlayer dielectric 69 is used to electrically isolate the coil from the first printed thermocouple element 12.

As will be apparent to those skilled in the art, the resistance of the heater element can be varied through trace thickness, width, bulk resistivity, or length as well as any combination thereof.

In another embodiment, the heated thermocouple device of the present invention can further comprise a voltage reader operably coupled to the electrical connectors to measure the voltage between the first and second printed thermocouple elements and to a voltage source operably coupled to the electrical connectors to apply current to the first and second printed thermocouple elements. Also, by providing switching and timing circuitry, the thermocouple device can alternatively be read as a temperature sensor and energized to provide localized heating.

Figure 10:
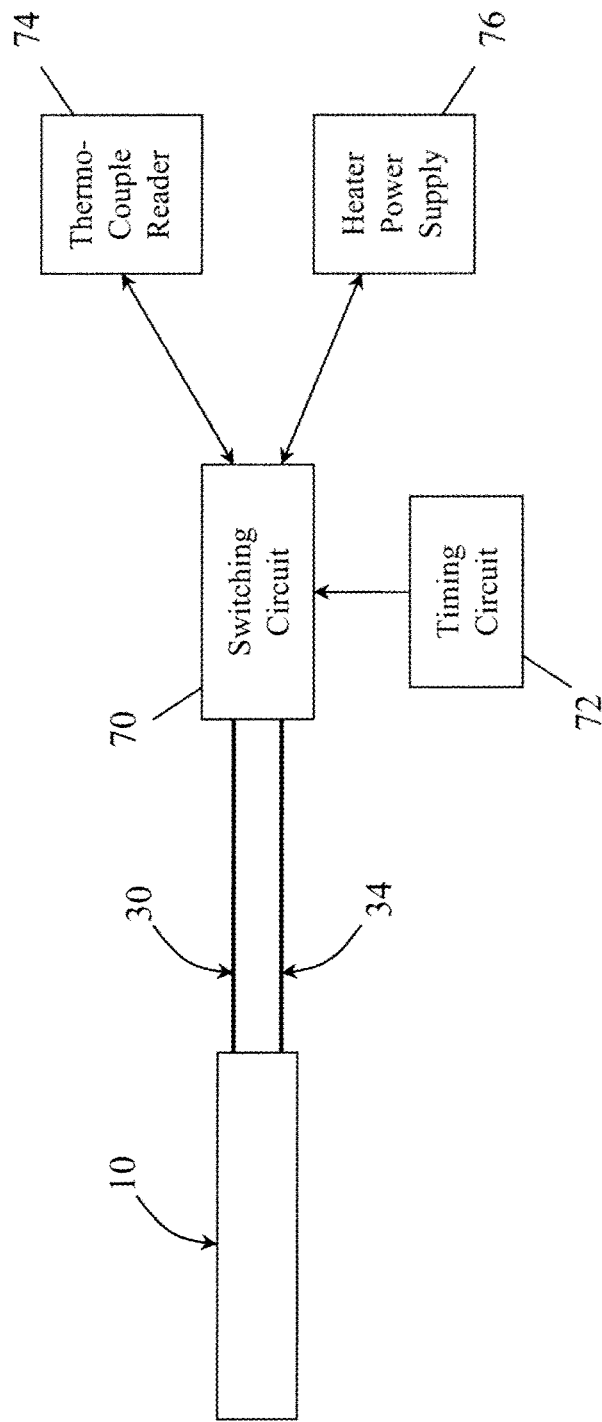
FIG. 10 shows a schematic diagram of the control elements couple to a heater thermocouple device that allows the device to act as a heater and as a thermocouple. For example, as shown here, the control elements include a thermocouple reader which could be used to provide a read out of the temperature detected by the thermocouple. Another control element which may be coupled to the heater thermocouple device is shown as the heater power supply. This heater power supply could be used, for example, to generate heat in the heater element of the thermocouple. An optional control element is shown as the switching circuit. This switching circuit could be functionally coupled to a timing circuit to permit suitably timed coupling of the thermocouple reader and the heater power supply to the heater thermocouple element.

In yet another embodiment, the heated thermocouple device of the present invention can comprise a switching module which selectively couples the electrical connectors of the first and second printed thermocouple elements to the voltage reader or the voltage source. Referring to FIG. 10, the thermocouple device 10 can be made to function as both a heater and a temperature sensor by connecting the first and second interconnection assemblies 30 and 34 to a switching circuit 70 which alternately connects the device to a thermocouple reader 74 to take temperature measurements or to a heater power supply 76 to excite the thermocouple device 10 to produce heat. A timing circuit 72 is utilized to control the switching circuit 70.

In another aspect, the present invention is related to a medical device comprising the thermocouple device of the present invention. For example, the medical device could be a three-dimensional polymeric medical device having a functional thermocouple applied directly and permanently on its surface by an industrial printing or direct-writing technique.

Medical devices are generally defined by the United States Food and Drug Administration as "an instrument, apparatus, implement, machine, contrivance, implant, in vitro reagent, or other similar or related article, including a component part, or accessory which is: 1) recognized in the official National Formulary, or the United States Pharmacopoeia, or any supplement to them; 2) intended for use in the diagnosis of disease or other conditions, or in the cure, mitigation, treatment, or prevention of disease, in man or other animals; or 3) intended to affect the structure or any function of the body of man or other animals, and which does not achieve any of it's primary intended purposes through chemical action within or on the body of man or other animals and which is not dependent upon being metabolized for the achievement of any of its primary intended purposes."

In another embodiment, the medical device of the present invention comprises a plurality of thermocouple junctions formed by a combination of a plurality of the printed thermocouple elements.

Figure 11:
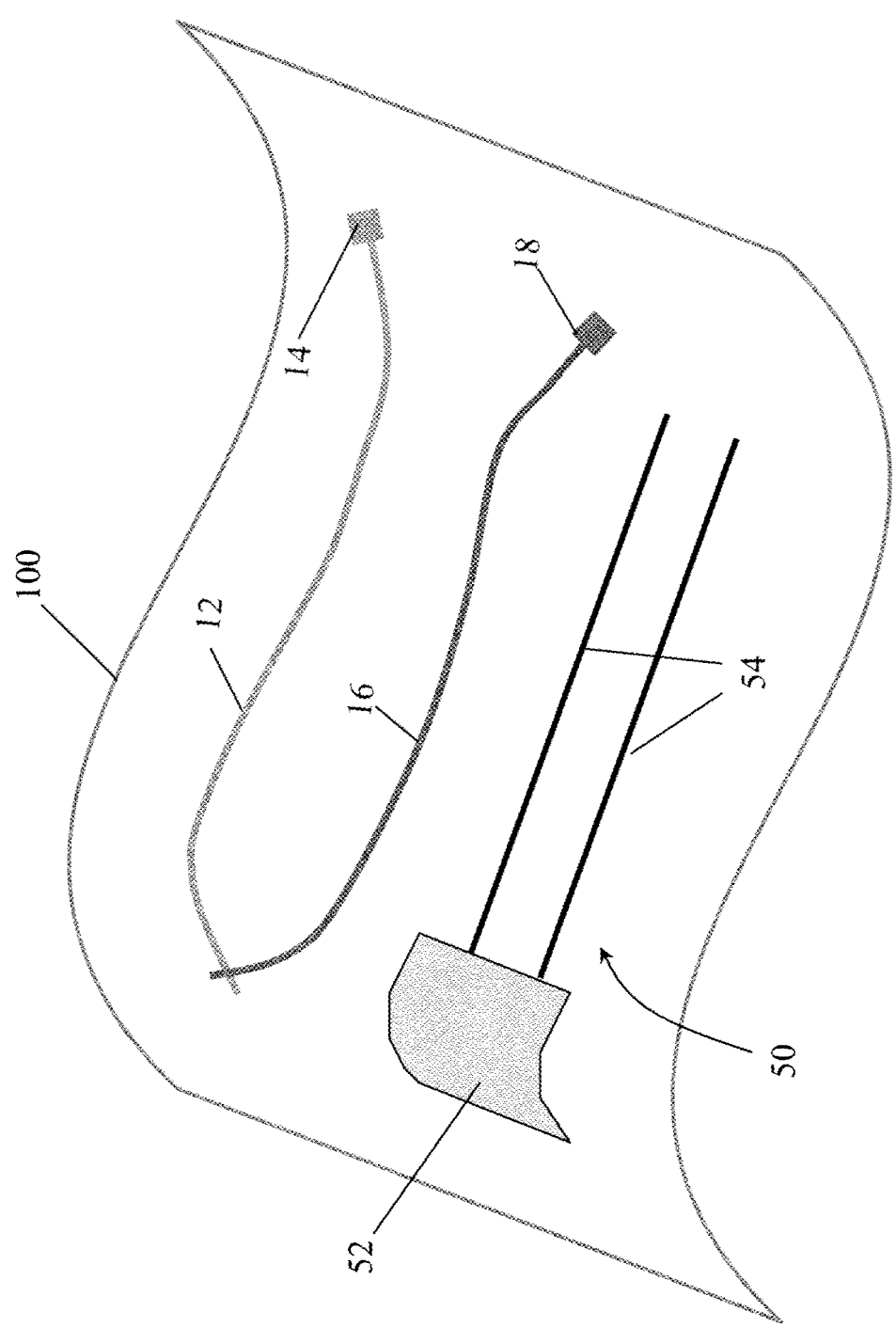
FIG. 11 shows a tilted top view of a secondary functional device disposed in close proximity to the thermocouple device. This secondary functional device is not necessarily printed on the substrate on which the thermocouple device is printed and can operate independently.

In yet another embodiment, the medical device of the present invention can be operably connected to another device to control or monitor the other device's function. Referring now to FIG. 11, a secondary functional device 50 may also be present simultaneously with thermocouple device 10. Secondary functional device 50 may include active element 52 and accompanying electrical leads 54. Some examples of secondary functional device 50 include: transducers to transmit electromagnetic fields, electromagnetic energy, heat, light, force, pressure, or medicaments to body tissues; sensors to detect electromagnetic fields, electromagnetic energy, light, force, pressure, pathogens, chemical species, or biological entities. Secondary functional device 50 and thermocouple device 10 may be in close proximity and may communicate thermally. Thermocouple device 10 may be used to monitor, control, or guide the use of secondary functional device 50. For example, thermocouple device 10 could be connected to a control system where a temperature set point acts as a trigger to turn secondary functional device 50 on or off. The presence or absence of any secondary devices, coatings, or other functional elements on the medical device is coincidental to the present invention.

The medical devices of the present invention include, but are not limited to, endotracheal tubes, endobronchial tubes, cannulae, catheters, balloons, stents, airways, sensors, stimulators, implants, intraocular or contact lenses, cochlear implants, and orthopedic implants or prostheses and the like. Sensors can include sensing capsules, stimulators, and the like. While drug-eluting stents or other drug-eluting devices do not strictly conform to the definition above, they are considered primarily as medical devices and therefore are encompassed by the present invention.

The measurement of temperature on the surface of such medical devices is extremely useful in a variety of situations. For example, core body temperature may be measured directly during a procedure without introducing an additional device. During radio frequency ablation procedures, the temperatures of the probe and surrounding tissue must be controlled so that unintended damage does not occur, and a thermocouple printed directly on an ablation device is useful in providing a feedback information for the cooling mechanism. Another useful application for thermocouples printed directly on medical devices is to provide a means of precisely detecting the location of cancerous lesions or areas of inflammation, since they exhibit higher temperatures than surrounding tissue.

Radiopaque traces may also be printed directly on the medical device of interest in order to accurately visualize its position during a procedure. In another non-limiting example, the thermocouple could be used to work as a heat source which controls the temperature requirements for functioning of a medical device or drug delivery agent.

A further aspect of the present invention relates to a method of forming a thermocouple device. The method comprises applying a first metal containing ink composition to a flexible non-planar substrate, where the first metal containing ink composition forms a first printed thermocouple element and applying a second metal containing ink composition to the first metal containing ink composition applied to the flexible non-planar substrate where the second metal containing ink composition forms a second printed thermocouple element. The first and second metal containing ink compositions have a Seebeck coefficient sufficiently different from one another so that the first and second printed thermocouple elements together produce a thermocouple effect.

Figure 12A:
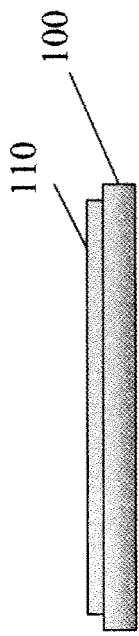
FIGS. 12A-E show cross-sectional views of the sequential fabrication steps that may be used in constructing a thermocouple device of the present invention. The steps shown on the left are cross sections along section AA in FIG. 1 and the steps shown on the right are cross sections along section AA in FIG. 2A.
Figure 12A:
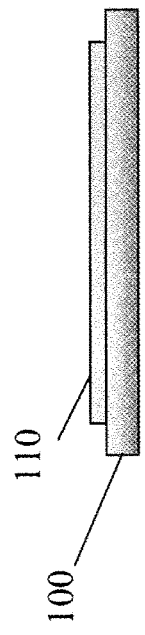

FIGS. 12A-E illustrate the fabrication sequence of thermocouple device 10. Note that the cross sections shown correspond to Section AA of FIG. 1 (see left side of FIG. 12) and Section AA of FIG. 2A (see right side of FIG. 12). FIG. 12A depicts the application of intermediate layer 110, which has been omitted in FIGS. 1 and 2. Intermediate layer 110 is an optional layer which may be used, for example, to: improve adhesion between medical device substrate 100 and the thermocouple materials; provide additional stiffening if medical device substrate 100 proves too flexible to adequately support the thermocouple traces; or provide electrical isolation if medical device substrate 100 possesses electronic or ionic conductivity such that it interferes with the proper functioning of thermocouple device 10. Note that for simplicity of presentation the presence of intermediate layer 110 is omitted in FIGS. 12B-E and all subsequent figures.

Figure 12B:
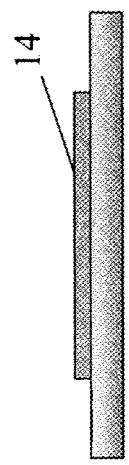
Figure 12B:
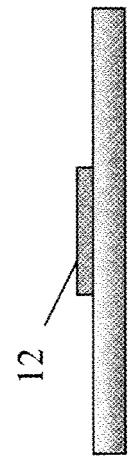

Referring to FIG. 12B, first printed thermocouple element 12 and first contact pad 14 are disposed on medical device substrate 100.

Figure 12C:
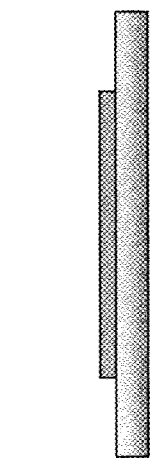
Figure 12C:
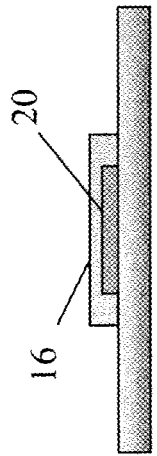

Referring to FIG. 12C, second printed thermocouple element 16 and first contact pad 18 (not observable in the cross-sectional views provided) are disposed on medical device substrate 100. The contact interface between the first and second thermocouple elements 12 and 16 forms the thermocouple junction 20.

Figure 12D:
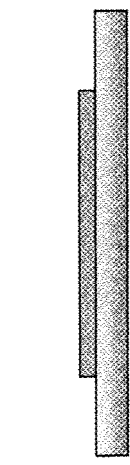
Figure 12D:
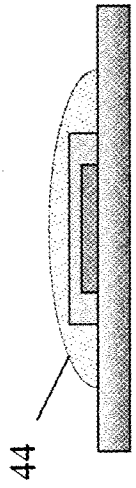

Referring to FIG. 12D, printed trace overcoat 44 is a dielectric layer disposed over the first and second thermocouple elements 12 and 16 but not the first and second contact pads 14 and 18. Printed trace overcoat 44 protects the printed elements from ions, moisture and friction and provides support against stress. Printed trace overcoat 44 can also provide a means for conduction of heat from the external medium to the thermocouple or be used as a means of enhancing flexibility and providing support to the device. Printed trace overcoat 44 may be laced with materials that impart desirable properties such as radio opacity, enhanced thermal conductivity, temperature controlled chemical release of medicaments, or the ability to carry other medical devices (e.g., a glucose meter). In addition, printed trace overcoat 44 ensures that any irritation or toxicity inherent to the metal or its binder is isolated from the body tissues. Any biocompatible, non-conductive, impermeable polymer which is easily applied may be used. Medical grade silicones, such as those provided by NuSil® (Bakersfield, Calif.), or medical grade acrylate adhesives, such as those provided by Dymax® (Torrington, Conn.), are particularly preferred. In order not to severely compromise the response time of the thermocouple, it is preferable to maximize the thermal conductance of any such overcoat layer, either by thinning the layer as much as possible, or by adding thermally conductive fillers which do not otherwise interfere with the function of the impermeable overcoat layer.

Figure 12E:
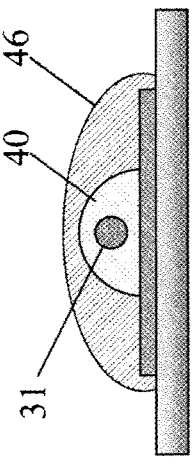

Referring to FIG. 12E, the formation of interconnections to thermocouple device 10 is accomplished by bringing first contact pad 14 into electrical communication with first conductor 31 through the use of first bonding material 40 which is subsequently cured in an appropriate fashion. Following the cure, interconnection overcoat 46 is applied to electrically isolate and hermetically seal the interconnection junction. Not shown in FIG. 12E is the subsequent and final step of connecting second contact pad 18 and providing an interconnection overcoat.

In one embodiment, the applying steps in forming the thermocouple device are carried out by direct writing. The applying steps may be independently carried out by screen printing, jetting, laser ablation, direct writing, or pressure driven syringe delivery.

Many direct writing techniques that satisfactorily control and manipulate the three dimensional, irregular substrate may be used for the purposes of the present invention, including screen printing, jetting, laser ablation, direct writing, or pressure driven syringe delivery, inkjet or aerosol jet droplet based deposition, laser or ion-beam material transfer, tip based deposition techniques such as dip pen lithography, or flow-based microdispensing (e.g., Micropen® [Micropen Technologies Corp., Honeoye Falls, N.Y.] or NScrypt® technologies). Such techniques are well described in Pique et al., *Direct-Write Technologies for Rapid Prototyping Applications: Sensors, Electronics, and Integrated Power Sources*, Academic Press (2002).

Microdispensing techniques such as Micropen® direct writing are particularly preferred for marking of medical devices, due to their ability to accommodate inks having an extremely wide range of rheological properties and very high solids levels, as well as excellent three dimensional substrate manipulation capabilities. To form the thermocouples on surfaces, a Micropen® can be used to apply the lines of the two or more selected thermo-element inks or paints such that they overlap at the location where the temperature is to be measured. These lines can then be extended to a convenient area where the thermocouple extension conductors can be attached to connect the cold junctions and instrumentation.

This technique is especially suited for flexible objects, as the writing force is continuously adjusted to compensate for substrate morphology, so that permanent deformation of the surface is not a concern. A major advantage of using a microdispensing technique to write the thermocouple elements is that the tip of the pen does not come in direct contact with the substrate during the writing process. This makes it a preferable method for writing thermocouple elements, because no distortion of the substrate is expected during the writing process.

When the junction is produced by a direct deposition technique, a liquid or paste ink is generally used. Usually metals, to be included in the ink, are selected from those already available in printable ink form or those that are available in a particulate form that can easily be dispersed into a printable ink or paste. Furthermore, wires comprised of the metals should also be readily formed or commercially available in order to form the leads to the measurement device and avoid the presence of a secondary junction. For example, nickel particles and inks are common and relatively inexpensive. Copper or tungsten inks and particles are also commonly available, as are noble metals such as silver, platinum, and palladium. Metallic alloys also may be produced in powder or flake form via atomization or attrition and then formulated into printable inks. For example, constantan, chromel, or alumel can be formed by spray atomization and then made into an ink intended to be used in a thermocouple.

EXAMPLES

Example 1—Method of Making the Thermocouple

Silver ink was prepared by dissolving poly(vinyl chloride) (high molecular weight, Sigma ALDRICH®) at a level of 13% by weight in a mixture of tetrahydrofuran, n-methyl pyrrolidone and α-terpineol in a ratio of 55:36:9 by weight. Silver flake (10 μm, >99.9%, SIGMA-ALDRICH®) was added to yield a ratio of silver:poly(vinyl chloride) of 85:15. The total solids were 50% by weight. In order to enable a thorough mixing, the materials were combined using a planetary high shear mixer (KURABO MAZERUSTAR KK-50S)

Nickel ink was prepared by dissolving poly(vinyl chloride) (high molecular weight, Sigma-ALDRICH® at a level of 13% by weight in a mixture of tetrahydrofuran, n-methyl pyrrolidone and α-terpineol in a ratio of 67.5:26:6.5 by weight. Nickel powder (3 μm, 99.7%, SIGMA-ALDRICH®) was added to yield a ratio of nickel:poly(vinyl chloride) of 85:15. The total solids were 44% by weight.

The inks were loaded into syringes and extruded through a MicroPen® direct writing device onto the surface of a commercially available standard endotracheal tube (UNO-MEDICAL® AIR MANAGEMENT, Magill, HVLP cuff) to yield two thermocouple junctions; one printed on the inflated cuff of the endotracheal tube and the other printed on the side of the tube itself just below the cuff (FIG. 1). The junctions were extended to allow for subsequent interconnection. The inks were then written and cured (forced air, 130° C., 1 hour) with silver followed by nickel.

After the metal junctions and leads were cured, they were covered, except for small connection pads at the end of each lead, with a UV-curable medical polymeric encapsulant (DYMAX 1-20323; DYMAX® Corporation) which was subsequently cured via ultraviolet irradiation.

After completion, nickel wire (SCIENTIFIC INSTRUMENT Services®, 0.5 mm diameter) was attached to the nickel leads and silver wire (Alfa Aesar, 0.5 mm diameter, 99.9%) to the silver leads; each bonded using its corresponding ink as an adhesive and cured at 100° C. for 1 hour in a forced air oven.

In order to test the temperature response of the printed thermocouples, the free leads were then attached to a thermocouple reader (Acromag® Model 965EN-4006) and the endotracheal tube placed in a programmable oven. The temperature was cycled from ambient 25° C. to 120° C. in 2 hours, then ramped back to room temperature at the same rate. Voltage data was collected using the LABVIEW® software program from 30° C. to 120° C. and back to 30° C. The heating and cooling rates were identical at 45° C./hour. Six data point was collected each minute of testing. For comparison, data was simultaneously collected for a commercially available Type K thermocouple (OMEGA ENGINEERING, Inc.®) placed in the oven near the tube.

The thermocouple junction on the tube was tested and a linear response was obtained for voltage vs temperature, yielding a slope of 20 µV/C. The data nearly precisely overlaid for both heating and cooling cycles. The temperature ramps were repeated and the data was duplicated.

Example 2—Testing of Cyclohexane as a Solvent to Prepare Thermocouple

Thermocouples were prepared in a manner identical to that described in Example 1, except the solvent used for the inks was cyclohexanone. Also, nickel flake (−325 mesh, 0.37 microns thick, 99.8%, Alfa Aesar®) was used instead of nickel powder, and the final percentage of solids of the nickel inks was adjusted to 46% by weight.

Junctions and traces were printed onto the surface of an endotracheal tube using Micropen® direct writing device as described in Example 1—i.e. cured, covered with a polymeric encapsulant, and leads attached as described previously.

The printed thermocouple junction on the tube was tested as described in Example 1, except in this case the maximum temperature was raised to 130° C., yielding a response of 20 µV/C for heating and cooling.

The thermocouple junction on the cuff was evaluated similarly, except the maximum temperature reached was 140° C. Also, after the heating cycle was completed, a cooling cycle was carried out in an environmental test chamber (Model BTRC, Tenney® Environmental) down to −40° C. Then, the temperature was raised back to room temperature. The data collected was linear, repeatable, and indicated a sensitivity of 18 µV/° C.

Example 3—Use of Commercially Available Metallic Inks to Make Thermocouples

Thermocouples were prepared identically to Example 1, except commercially available metallic inks were use. The silver ink used was 101-59 (Creative Materials, Inc. (Tyngsboro, Mass.)) and the nickel inks used was 116-25 (Creative Materials, Inc. (Tyngsboro, Mass.)). The nickel ink was bonded to the nickel wire using the nickel ink as an adhesive; and the silver wire was bonded using a silver epoxy (Epo-Tek® H20E; Epoxy Technology, Inc (Billerica, Mass.)).

A thermocouple junction positioned on the cuff was evaluated on heating and cooling from 25° C. to 145° C. and back, and had a sensitivity of 20 µV/° C.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

PARTS LIST 10 thermocouple device
11 substantially cylindrical thermocouple device
12 first printed thermocouple element
14 first contact pad
16 second printed thermocouple element
18 second contact pad
20 thermocouple junction
21 heater section connection
22 second thermocouple junction
24 third thermocouple junction
30 first interconnection assembly
31 first conductor
32 first insulator
34 second interconnection assembly
35 second conductor
36 second insulator
38 third interconnection assembly
40 first bonding material
42 second bonding material
44 printed trace overcoat
46 interconnection overcoat
50 secondary functional device
52 active element
54 electrical leads
60 heater section
62 heater section based on trace thickness
64 heater section based on trace width
66 heater section based on material formulation
68 heater section based on trace length
69 interlayer dielectric
70 switching circuit
72 timing circuit
74 thermocouple reader
76 heater power supply
78 RF power supply
80 third printed thermocouple element
82 third contact pad
84 fourth printed thermocouple element
86 fourth contact pad
90 common lead contact pad
100 medical device substrate
102 substantially cylindrical medical device substrate
110 intermediate layer
200 three-terminal thermocouple device

What is claimed:

1. A thermocouple device comprising:
   a medical device comprising a polymer substrate comprising a substantially tubular portion;
   a first thermocouple element printed directly on the substantially tubular portion, the first thermocouple element comprising a first metal containing ink composition comprising a polymeric binder and metallic particles; and
   a second printed thermocouple element in electrical contact with the first printed thermocouple element making a thermocouple junction, the second printed thermocouple element comprising a second metal containing ink composition comprising a polymeric binder and metallic particles with a Seebeck coefficient sufficiently different from the first metal containing ink composition for the first and second printed thermocouple elements to together produce a thermocouple effect,
   wherein a portion of the first printed thermocouple element is linear and the second printed thermocouple element conforms to the substantially tubular portion, and
   wherein the polymeric binders of the first and second ink compositions are entangled with the substrate.

2. The thermocouple device according to claim 1, wherein the second printed thermocouple element forms a solenoid coil around the substantially tubular portion.

3. The thermocouple device according to claim 1, wherein the substantially tubular portion has an irregular surface.

4. The thermocouple device according to claim 1, further comprising:

electrical connectors electrically coupled to the first and second printed thermocouple elements.

5. The thermocouple device according to claim 4 further comprising:
a voltage reader operably coupled to the electrical connectors to measure the voltage between the first and second printed thermocouple elements.

6. The thermocouple device according to claim 4 further comprising:
a voltage source operably coupled to the electrical connectors to apply current to the first and second printed thermocouple elements.

7. The thermocouple device according to claim 1 further comprising:
an overcoat layer covering the first and second printed thermocouple elements.

8. The thermocouple device according to claim 7, wherein the overcoat layer is formed from a material selected from the group consisting of epoxy, polyacrylate, silicone or natural rubber, polyester, polyethylene napthalate, polypropylene, polycarbonate, polystyrene, polyvinyl fluoride, ethyl-vinyl acetate, ethylene acrylic acid, acetyl polymer, poly(vinyl chloride), silicone, polyurethane, polyisoprene, styrene-butadiene, acrylonitrile-butadiene-styrene, polyethylene, polyamide, polyether-amide, polyimide, polyetherimide, polyetheretherketone, polyvinylidene chloride, polyvinylidene fluoride, polycarbonate, polysulfone, polytetrafuoroethylene, polyethylene terephthalate, polyhydroxyalkanoate, poly(p-xylylene), liquid crystal polymer, polymethylmethacrylate, polyhydroxyethylmethacrylate, polylactic acid, polyhydroxyvalerate, polyvinyl chloride, polyphosphazene, poly(ε-caprolactone) and mixtures or copolymers thereof.

9. The thermocouple device according to claim 1, wherein the first and second metal containing ink compositions independently comprise a metal powder selected from the group consisting of copper, palladium, chromel, alumel, rhenium, nickel-chromium-silicon, constantan, cadmium, aluminum, platinum, rhodium, iridium, molybdenum, tantalum, beryllium, zinc, tin, chromium, nickel, nickel-chromium, nickel-aluminum, nickel-silicon, iron, tungsten, lead, silver, gold, magnesium, silicon or alloys thereof.

10. The thermocouple device according to claim 1, wherein the first and second printed thermocouple elements collectively have a thickness of 0.1 to 500 microns.

11. The thermocouple device according to claim 10, wherein the first and second printed thermocouple elements collectively have a thickness of 12 to 80 microns.

12. The thermocouple device according to claim 1 comprising a plurality of thermocouple junctions formed by a combination of a plurality of printed thermocouple elements.

13. The thermocouple device according to claim 4 further comprising:
a voltage reader operably coupled to the electrical connectors to measure the voltage between the first and/or second printed thermocouple elements and
a radio frequency module operably coupled to the electrical connectors of the first and/or second printed thermocouple elements to generate radio frequency waves or to detect radio frequency waves.

14. The thermocouple device according to claim 13, wherein the radio frequency module can be a radio frequency generator, radio frequency detector, or a combination thereof.

15. The thermocouple device according to claim 13 further comprising:
a switching module which selectively couples the electrical connectors of the first and/or second printed thermocouple elements to the voltage reader or the radio frequency module.

16. The thermocouple device according to claim 13, wherein the electrical connectors of the first and/or second printed thermocouple elements are permanently connected to the voltage reader and the radio frequency module.

17. A system comprising:
the thermocouple device according to claim 1 and
another device, wherein the thermocouple device is operably connected to the another device to control or monitor the another device's function.

18. The device according to claim 1, wherein the medical device is selected from the group consisting of endotracheal tubes, endobronchial tubes, cannulae, catheters, balloons, stents, airways, sensors, stimulators, implants, cochlear implants, and orthopedic implants or prostheses.

19. The thermocouple device according to claim 1, wherein the substantially tubular portion is flexible.

20. The thermocouple device according to claim 1, wherein the medical device is a catheter.

21. The thermocouple device according to claim 1, wherein at least a portion of the second printed thermocouple element is of a different thickness than the first printed thermocouple element.

22. The thermocouple device according to claim 1, wherein at least a portion of the second printed thermocouple element is of a different width than the first printed thermocouple element.

23. A heated thermocouple device comprising:
a medical device comprising a polymer substrate comprising a substantially tubular portion;
a first thermocouple element printed directly on the substantially tubular portion, the first thermocouple element comprising a first metal containing ink composition comprising a polymeric binder and metallic particles;
a second printed thermocouple element applied to the substantially tubular portion and comprising a second metal containing ink composition comprising a polymeric binder and metallic particles with a Seebeck coefficient sufficiently different from the first metal containing ink composition for the first and second printed thermocouple elements to together produce a thermocouple effect, wherein a portion of the first printed thermocouple element is linear and the second printed thermocouple element conforms to the substantially tubular portion; and
a heater element applied to the substantially tubular portion and comprising a third metal containing ink composition comprising a polymeric binder and metallic particles, wherein said heater element is electrically connected to the first and second printed thermocouple elements, wherein the polymeric binders of the first and second ink compositions are entangled with the substrate.

24. The thermocouple device according to claim 23, wherein the second printed thermocouple element forms a solenoid coil around the substantially tubular portion.

25. The heated thermocouple device according to claim 23 further comprising:
electrical connectors coupled to the first and second printed thermocouple elements.

26. The heated thermocouple device according to claim 23 further comprising:

a voltage reader operably coupled to the electrical connectors to measure the voltage between the first and second printed thermocouple elements and a voltage source operably coupled to the electrical connectors to apply current to the first and second printed thermocouple elements.

27. The heated thermocouple device according to claim 26 further comprising:

a switching module which selectively couples the electrical connectors of the first and second printed thermocouple elements to the voltage reader or the voltage source.

28. The thermocouple device according to claim 23, wherein at least a portion of the second printed thermocouple element is of a different thickness than the first printed thermocouple element.

29. The thermocouple device according to claim 23, wherein at least a portion of the second printed thermocouple element is of a different width than the first printed thermocouple element.

\* \* \* \* \*